US011566068B2

(12) United States Patent
Leow et al.

(10) Patent No.: US 11,566,068 B2
(45) Date of Patent: Jan. 31, 2023

(54) NUCLEIC ACIDS ENCODING BISPECIFIC ANTI-VEGF AND ANTI-ANG2 ANTIBODIES AND USES THEREOF

(71) Applicant: MEDIMMUNE LIMITED, Cambridge (GB)

(72) Inventors: Ching Ching Leow, Gaithersburg, MD (US); Nazzareno Dimasi, Gaithersburg, MD (US); Karen Coffman, Gaithersburg, MD (US); Ryan Fleming, Gaithersburg, MD (US); Ping Tsui, Gaithersburg, MD (US); Changshou Gao, Gaithersburg, MD (US); Mario A. Cepeda, Winchester, MA (US); Adrian Schwartz Mittelman, Brookfield, CT (US)

(73) Assignee: MEDIMMUNE LIMITED, Cambridge (GB)

( * ) Notice: Subject to any disclaimer, the term of this patent is extended or adjusted under 35 U.S.C. 154(b) by 243 days.

(21) Appl. No.: 17/070,157

(22) Filed: Oct. 14, 2020

(65) Prior Publication Data
US 2021/0040194 A1 Feb. 11, 2021

Related U.S. Application Data

(62) Division of application No. 16/327,207, filed as application No. PCT/EP2017/071104 on Aug. 22, 2017, now Pat. No. 10,836,819.

(60) Provisional application No. 62/378,388, filed on Aug. 23, 2016.

(51) Int. Cl.
*C07K 16/22* (2006.01)
*C12N 15/13* (2006.01)
*C12N 15/85* (2006.01)
*A61K 39/00* (2006.01)

(52) U.S. Cl.
CPC .............. *C07K 16/22* (2013.01); *C12N 15/85* (2013.01); *A61K 2039/505* (2013.01); *C07K 2317/31* (2013.01); *C07K 2317/35* (2013.01); *C07K 2317/92* (2013.01); *C12N 2015/8518* (2013.01)

(58) Field of Classification Search
None
See application file for complete search history.

(56) References Cited

U.S. PATENT DOCUMENTS

2016/0215045 A1 7/2016 Leung et al.

FOREIGN PATENT DOCUMENTS

| CN | 101370519 | 2/2009 |
| CN | 102250248 | 11/2011 |
| CN | 102753577 | 10/2012 |
| CN | 102906114 | 1/2013 |
| CN | 103906533 | 7/2014 |
| CN | 104428315 | 3/2015 |
| CN | 105085678 | 11/2015 |
| KR | 1020150063847 A | 6/2015 |
| WO | WO-2006/068953 | 6/2006 |
| WO | WO-2009/097325 | 8/2009 |
| WO | WO-2010/040508 | 4/2010 |
| WO | WO-2011/117329 | 9/2011 |
| WO | WO-2012/131078 | 10/2012 |
| WO | WO-2013/070565 | 5/2013 |
| WO | WO-2014/009465 | 1/2014 |
| WO | WO-2015/171747 A1 | 11/2015 |
| WO | WO-2016/075037 | 5/2016 |
| WO | WO-2016/122996 | 8/2016 |

OTHER PUBLICATIONS

Guo et al., "Progress In research of bispecific antibody drugs", Chinese Journal of New Drugs, 2016, vol. 25, No. 05, pp. 518-523 (Abstract Only).
Kloepper et al., "Ang-2/VEGF bispecific antibody reprograms macrophages and resident microglia to anti-tumor phenotype and prolongs glioblastoma survival", PNAS, Apr. 19, 2016, vol. 113, No. 16, pp. 4476-4481.
Lin et al., "Identification of a Neutralizing ScFv Binding to Human Vascular Endothelial Growth Factor 165 (VEGF165) Using a Phage Display Antibody Library," Appl Biochem Biotechnol (2008) vol. 144, pp. 15-26.
Dimasi et al., "The Design and Characterization of Oligospecific Antibodies for Simultaneous Targeting of Multiple Disease Mediators," Journal of Molecular Biology, Academic Press, United Kingdom, vol. 393, No. 3, Oct. 30, 2009, pp. 672-692.
Ferrara et al., "Bevacizumab (Avast in), a humanized anti-VEGF monoclonal antibody for cancer therapy," Biochemical and Biophysical Research Communications, Elsevier, Amsterdam, NL, vol. 333, No. 2, Jul. 29, 2005 , pp. 328-335.
Houck et al., "The Vascular Endothelial Growth Factor Family: Identification of a Fourth Molecular Species and Characterization of Alternative Splicing of RNA," Molecular Endocrinology, The Endocrine Society, US, vol. 5, No. 12, Dec. 1, 1991, pp. 1806-1814.
Jendreyko et al., "Simultaneous, phenotypic knockout of VEGF-R2 and Tie-2 with an intradiabody enhances antiangiogenic effects in vivo," Klinische Paediat, Ferdinand Enke Verlag, Stuttgart, DE, vol. 218, No. 3, May 1, 2006, pp. 143-151.
Leow at al., "MEDI3617, a human anti-angiopoietin 2 monoclonal antibody, inhibits angiogenesis and tumor growth in human tumor xenograft models," International Journal of Oncology, Demetrios A. Spandidos Ed. & Pub, GR, vol. 40, No. 5, May 1, 2012, pp. 1321-1330.

(Continued)

*Primary Examiner* — Christine J Saoud
*Assistant Examiner* — Jon M Lockard
(74) *Attorney, Agent, or Firm* — Foley & Lardner LLP

(57) ABSTRACT

The present invention relates to bispecific antibodies having activity against a vascular endothelial growth factor (VEGF) and an angiopoietin (ANG), and methods of making and using such bispecific antibodies.

4 Claims, 21 Drawing Sheets
Specification includes a Sequence Listing.

(56) References Cited

OTHER PUBLICATIONS

Liang Wei-Ching et al., "Cross-species vascular endothelial growth factor (VEGF)-blocking antibodies completely inhibit the growth of human tumor xenografts and measure the contribution of stromal VEGF,"Journal of Biological Chemistry, American Society for Biochemistry and Molecular Biology, vol. 281, No. 2, Nov. 7, 2005, pp. 951-961.
Sachsenmeier et al., "Abstract 4635: The avidity hypothesis: comparing bispecific and monospecific antibodies in preclinical oncology models," Cancer Research, Apr. 1, 2013, pp. 1-3.
Kienast et al., "Ang-2-VEGF-A CrossMab, a Novel Bispecific Human IgG1 Antibody Blocking VEGF-A and Ang-2 Functions Simultaneously, Mediates Potent Antitumor, Antiangiogenic, and Antimetastatic Efficacy," Clinical Cancer Research, (Oct. 4, 2013), vol. 19, No. 24, pp. 6730-6740.
Byrne et al., A tale of two specificities: bispecific antibodies for therapeutic and diagnostic applications, Cell Press, vol. 31, No. 11, Nov. 2013, 12 pages.

FIG. 1
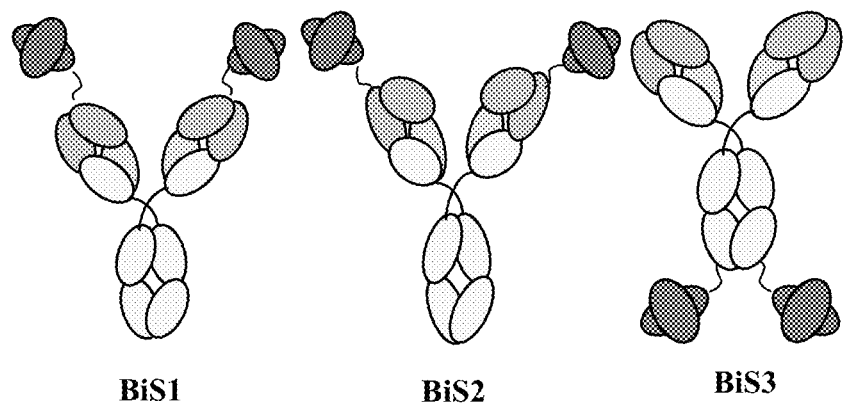
BiS1　　　BiS2　　　BiS3
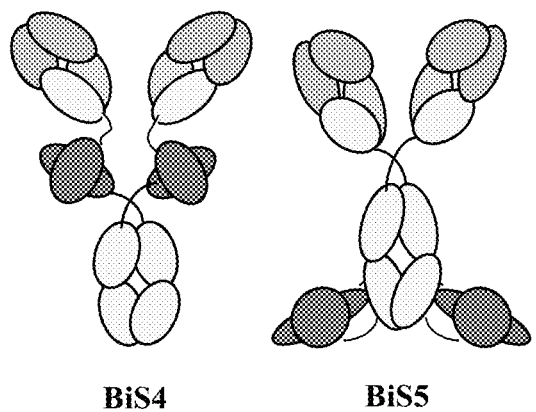
BiS4　　　BiS5

FIG. 3

*(SEQ ID NO: 29) >DNA sequence: light chain variable domain and constant kappa of the domain Fab binding unit 1 (anti-VEGF) as shown in Figure 1*
GAGATCGTGCTGACCCAGTCTCCAGCCACCCTCTCTTTGTCTCCAGGGGAAAGAGCCACCCT
CTCCTGCAGGGCCAGTCAGAGTGTTCACAGCAGCTACTTAGCCTGGTACCAGCAGAAACCTG
GCCAGGCTCCCAGGCTCCTCATCTATGGTGCATCCAGCAGGGCCACTGGCATCCCAGACAGG
TTCAGTGGCAGTGGGTCTGGGACAGACTTCACTCTCACCATCAGCAGACTGGAGCCTGAAGA
TTTTGCAGTTTACTACTGTCAACAGAGTTACCGCACCCCTTCCTTCGGCCAAGGGACACGAC
TGGAGATTAAACGTACGGTGGCTGCACCATCTGTCTTCATCTTCCCGCCATCTGATGAGCAG
TTGAAATCTGGAACTGCCTCTGTTGTGTGCCTGCTGAATAACTTCTATCCCAGAGAGGCCAA
AGTACAGTGGAAGGTGGATAACGCCCTCCAATCGGGTAACTCCCAGGAGAGTGTCACAGAGC
AGGACAGCAAGGACAGCACCTACAGCCTCAGCAGCACCCTGACGCTGAGCAAAGCAGACTAC
GAGAAACACAAAGTCTACGCCTGCGAAGTCACCCATCAGGGCCTGAGCTCGCCCGTCACAAA
GAGCTTCAACAGGGGAGAGTGT

*(SEQ ID NO: 7) >Protein sequence: light chain variable domain and constant kappa of the domain Fab binding unit 1 (anti- VEGF)*
EIVLTQSPATLSLSPGERATLSCRASQSVHSSYLAWYQQKPGQAPRLLIYGASSRATGIPDR
FSGSGSGTDFTLTISRLEPEDFAVYYCQQSYRTPSFGQGTRLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC

*(SEQ ID NO: 9) >Protein sequence: light chain variable of the domain binding unit 1 (VL) (anti-VEGF)*
EIVLTQSPATLSLSPGERATLSCRASQSVHSSYLAWYQQKPGQAPRLLIYGASSRATGIPDR
FSGSGSGTDFTLTISRLEPEDFAVYYCQQSYRTPSFGQGTRLEIK

FIG. 4

(SEQ ID NO: 30) >DNA sequence: VH-CH1 domain of the Fab binding unit 1 (VEGF), FC region, connecting linkers as shown in Figure 1 and scFv of binding unit 2 (anti-Ang2)

GAAGTTCAATTGTTAGAGTCTGGTGGCGGTCTTGTTCAGCCTGGTGGTTCTTTACGTCTTTCT
TGCGCTGCTTCCGGATTCACTTTCTCTTGGTACGAGATGTATTGGGTTCGCCAAGCTCCTGGT
AAAGGTTTGGAGTGGGTTTCTTCTATCTCTCCTTCTGGTGGCTGGACTATGTATGCTGACTCC
GTTAAAGGTCGCTTCACTATCTCTAGAGACAACTCTAAGAATACTCTACTTGCAGATGAAC
AGCTTAAGGGCTGAGGACACGGCCGTGTATTACTGTGCGACCCCCTTGTATAGCAGTGACGGG
CTTTCGGCGGGGGATATCTGGGGCCAAGGGACAATGGTCACCGTCTCAAGCGCGTCGACCAAG
GGCCCATCCGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCCTGGAACTCAGGCGCTCTG
ACCAGCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATCACAAG
CCCAGCAACACCAAGGTGGACAAGAGAGTTGAGCCCAAATCTTGTGACAAAACTCACACATGC
CCACCGTGCCCAGCACCTGAACTCCTGGGGGGACCGTCAGTCTTCCTCTTCCCCCCAAAACCC
AAGGACACCCTCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAATGCCAAGACA
AAGCCGCGGGAGGAGCAGTACAACAGCACGTACCGTGTGGTCAGCGTCCTCACCGTCCTGCAC
CAGGACTGGCTGAATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGTCTACACCCTGCCC
CCATCCCGGGAGGAGATGACCAAGAACCAGGTCAGCCTGACCTGCCTGGTCAAAGGCTTCTAT
CCCAGCGACATCGCCGTGGAGTGGGAGAGCAATGGGCAGCCGGAGAACAACTACAAGACCACG
CCTCCCGTGCTGGACTCCGACGGCTCCTTCTTCCTCTATAGCAAGCTCACCGTGGACAAGAGC
AGGTGGCAGCAGGGGAACGTCTTCTCATGCTCCGTGATGCATGAGGCTCTGCACAACCACTAC
ACGCAGAAGAGCCTCTCCCTGTCTCCGGGTAAAGGCGGAGGGGGATCCGGCGGAGGGGGCTCT
GAGATCGTGCTGACCCAGAGCCCCGGCACCCTGAGCCTGAGCCCTGGCGAGAGAGCCACCCTG
AGCTGCCGGGCCAGCCAGTCCATCACCGGCAGCTACCTGGCTTGGTATCAGCAGAAGCCCGGA
CAGGCCCCCAGACTGCTGATCACCGGCGCTTCCAGCTGGGCCACCGGCATCCCCGACAGATTC
AGCGGCAGCGGCTCCGGCACCGACTTCACCCTGACCATCAGCAGACTGGAGCCCGAGGACTTC
GCCGTGTACTACTGCCAGCAGTACAGCAGCAGCCCCATCACCTTCGGAtgcGGCACCAGGCTG
GAGATCAAGGGCGGAGGGGGCTCTGGGGGAGGGGGCAGCGGCGGCGGAGGATCTGGGGGAGGG
GGCAGCCAGGTGCAGCTGGTCGAGTCTGGCGGCGGAGTGGTGCAGCCCGGCAGAAGCCTGAGA
CTGAGCTGCGCCGCCAGCGGCTTCACCTTCACCAACTACGGCATGCACTGGGTCCGCCAGGCC
CCTGGCAAGtGCCTGGAGTGGGTGGCCGTGATCAGCCACGACGGCAACAACAAGTACTACGTG
GACAGCGTGAAGGGCAGATTCACCATCAGCAGGGACAACAGCAAGAACACCCTGTACCTCCAG
ATGAACAGCCTGAGAGCCGAGGACACCGCCGTGTACTACTGCGCCAGAGAGGGCATCGACTTT
TGGAGCGGCCTGAATTGGTTCGACCCCTGGGGCCAGGGCACCCTGGTGACCGTGTCCAGC

FIG. 5

*(SEQ ID NO: 31) >Protein sequence: VH-CH1 domain of the Fab forming binding unit 1 (VEGF),FC region, connecting linkers as shown in Figure 1 and scFv of binding unit 2 (anti-Ang2)*
EVQLLESGGGLVQPGGSLRLSCAASGFTFSWYEMYWVRQAPGKGLEWVSSISPSGGWTMYADSVKGRF
TISRDNSKNTLYLQMNSLRAEDTAVYYCATPLYSSDGLSAGDIWGQGTMVTVSSASTKGPSVFPLAPS
SKSTSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGKGGGGSGGGGSEIVLTQSPGTLSLS
PGERATLSCRASQSITGSYLAWYQQKPGQAPRLLITGASSWATGIPDRFSGSGSGTDFTLTISRLEPE
DFAVYYCQQYSSSPITFGCGTRLEIKGGGGSGGGGSGGGGSGGGGSQVQLVESGGGVVQPGRSLRLSC
AASGFTFTNYGMHWVRQAPGKCLEWVAVISHDGNNKYYVDSVKGRFTISRDNSKNTLYLQMNSLRAED
TAVYYCAREGIDFWSGLNWFDPWGQGTLVTVSS

*(SEQ ID NO: 3) >Protein sequence: VH domain of the Fab forming binding unit 1 (anti-VEGF)*
EVQLLESGGGLVQPGGSLRLSCAASGFTFSWYEMYWVRQAPGKGLEWVSSISPSGGWTMYADSVKGRF
TISRDNSKNTLYLQMNSLRAEDTAVYYCATPLYSSDGLSAGDIWGQGTMVTVSS

*(SEQ ID NO: 32) >Protein sequence: heavy constant regions*
ASTKGPSVFPLAPSSKSTSGGTAALGCLVKDYFPEPVTVSWNSGALTSGVHTFPAVLQSSGLYSLSSV
VTVPSSSLGTQTYICNVNHKPSNTKVDKRVEPKSCDKTHTCPPCPAPELLGGPSVFLFPPKPKDTLMI
SRTPEVTCVVVDVSHEDPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSLSPGK

*(SEQ ID NO: 16) >Protein sequence: Glycine-Serine linker $(G_4S)_2$*
GGGGSGGGGS

*(SEQ ID NO: 13) >Protein sequence: scFv of binding unit 2 (anti-Ang2)*
EIVLTQSPGTLSLSPGERATLSCRASQSITGSYLAWYQQKPGQAPRLLITGASSWATGIPDRFSGSGS
GTDFTLTISRLEPEDFAVYYCQQYSSSPITFGCGTRLEIKGGGGSGGGGSGGGGSGGGGSQVQLVESG
GGVVQPGRSLRLSCAASGFTFTNYGMHWVRQAPGKCLEWVAVISHDGNNKYYVDSVKGRFTISRDNSK
NTLYLQMNSLRAEDTAVYYCAREGIDFWSGLNWFDPWGQGTLVTVSS

*(SEQ ID NO: 11) >Protein sequence: VL domain of binding unit 2 (anti-Ang2)*
EIVLTQSPGTLSLSPGERATLSCRASQSITGSYLAWYQQKPGQAPRLLITGASSWATGIPDRFSGSGS
GTDFTLTISRLEPEDFAVYYCQQYSSSPITFGCGTRLEIK

*(SEQ ID NO: 15) >Protein sequence: Glycine-Serine linker $(G_4S)_4$*
GGGGSGGGGSGGGGSGGGGS

*(SEQ ID NO: 5) >Protein sequence: VH domain of binding unit 2 (anti-Ang2)*
QVQLVESGGGVVQPGRSLRLSCAASGFTFTNYGMHWVRQAPGKCLEWVAVISHDGNNKYYVDSVKGRF
TISRDNSKNTLYLQMNSLRAEDTAVYYCAREGIDFWSGLNWFDPWGQGTLVTVSS

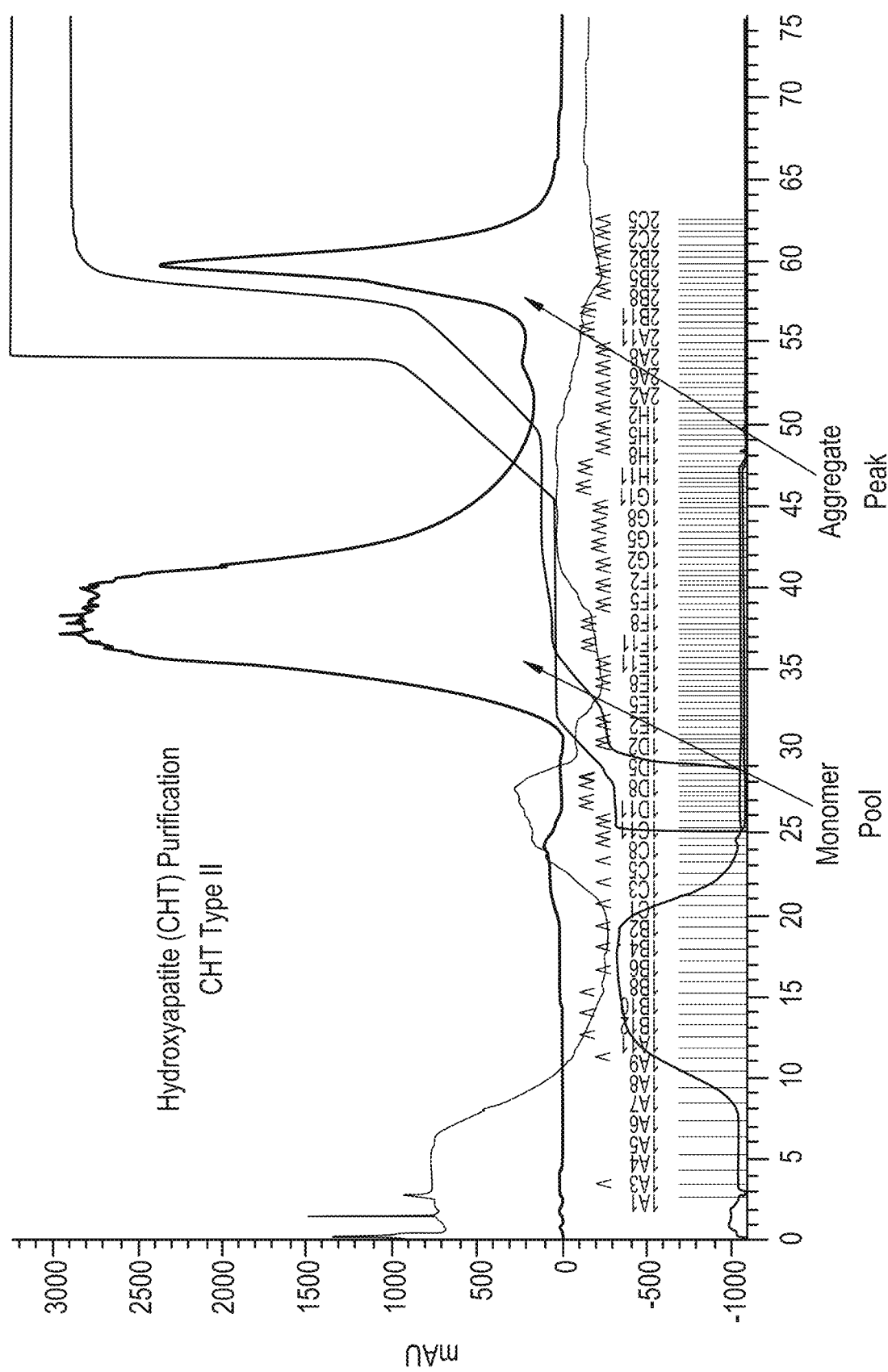

FIG. 19
Untreated
BiSAb-VEGF H1RK-ANG-2
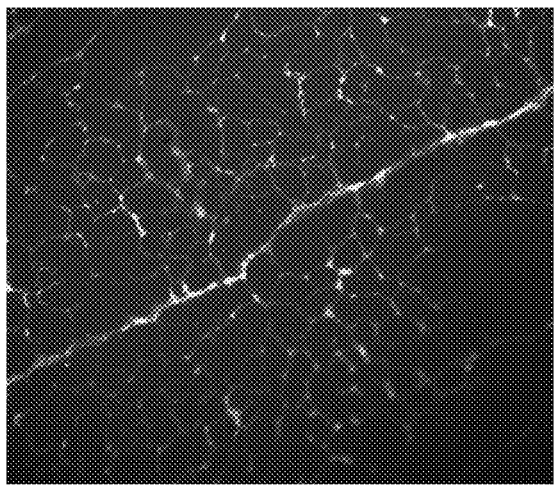
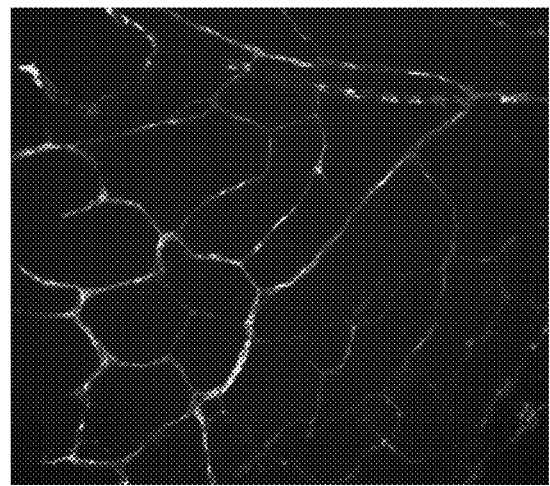

SEQUENCE LISTING

```
<160> NUMBER OF SEQ ID NOS: 32

<210> SEQ ID NO 1
<211> LENGTH: 713
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1
```

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Trp Tyr
             20                  25                  30

Glu Met Tyr Trp Val Arg Gln Ala Pro Gly Lys Gly Leu Glu Trp Val
         35                  40                  45

Ser Ser Ile Ser Pro Ser Gly Gly Trp Thr Met Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys Gly Gly Gly Ser Gly Gly Gly Ser Glu Ile
    450                 455                 460

Val Leu Thr Gln Ser Pro Gly Thr Leu Ser Leu Ser Pro Gly Glu Arg
465                 470                 475                 480

Ala Thr Leu Ser Cys Arg Ala Ser Gln Ser Ile Thr Gly Ser Tyr Leu
                485                 490                 495

Ala Trp Tyr Gln Gln Lys Pro Gly Gln Ala Pro Arg Leu Leu Ile Thr
            500                 505                 510

Gly Ala Ser Ser Trp Ala Thr Gly Ile Pro Asp Arg Phe Ser Gly Ser
        515                 520                 525

Gly Ser Gly Thr Asp Phe Thr Leu Thr Ile Ser Arg Leu Glu Pro Glu
    530                 535                 540

Asp Phe Ala Val Tyr Tyr Cys Gln Gln Tyr Ser Ser Pro Ile Thr
545                 550                 555                 560

Phe Gly Cys Gly Thr Arg Leu Glu Ile Lys Gly Gly Gly Ser Gly
                565                 570                 575

Gly Gly Gly Ser Gly Gly Gly Ser Gly Gly Gly Ser Gln Val
            580                 585                 590

Gln Leu Val Glu Ser Gly Gly Val Val Gln Pro Gly Arg Ser Leu
        595                 600                 605

Arg Leu Ser Cys Ala Ala Ser Gly Phe Thr Phe Thr Asn Tyr Gly Met
    610                 615                 620

His Trp Val Arg Gln Ala Pro Gly Lys Cys Leu Glu Trp Val Ala Val
625                 630                 635                 640

Ile Ser His Asp Gly Asn Asn Lys Tyr Tyr Val Asp Ser Val Lys Gly
                645                 650                 655

Arg Phe Thr Ile Ser Arg Asp Asn Ser Lys Asn Thr Leu Tyr Leu Gln
            660                 665                 670

Met Asn Ser Leu Arg Ala Glu Asp Thr Ala Val Tyr Tyr Cys Ala Arg
        675                 680                 685

Glu Gly Ile Asp Phe Trp Ser Gly Leu Asn Trp Phe Asp Pro Trp Gly
    690                 695                 700

Gln Gly Thr Leu Val Thr Val Ser Ser
705                 710

<210> SEQ ID NO 2
<211> LENGTH: 2139
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 2
gaagttcaat tgttagagtc tggtggcggt cttgttcagc ctggtggttc tttacgtctt    60
tcttgcgctg cttccggatt cactttctct tggtacgaga tgtattgggt tcgccaagct   120
cctggtaaag gtttggagtg ggtttcttct atctctcctt ctggtggctg gactatgtat   180
gctgactccg ttaaaggtcg cttcactatc tctagagaca actctaagaa tactctctac   240
ttgcagatga acagcttaag ggctgaggac acggccgtgt attactgtgc gaccccttg    300

-continued

```
tatagcagtg acgggctttc ggcgggggat atctggggcc aagggacaat ggtcaccgtc    360
tcaagcgcgt cgaccaaggg cccatccgtc ttccccctgg cacccctcctc caagagcacc    420
tctgggggca cagcggccct gggctgcctg gtcaaggact acttccccga accggtgacg    480
gtgtcctgga actcaggcgc tctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccaaat cttgtgacaa aactcacaca tgcccaccgt gcccagcacc tgaactcctg    720
ggggaccgt cagtcttcct cttccccca aacccaagg acaccctcat gatctcccgg       780
accctgagg tcacatgcgt ggtggtggac gtgagccacg aagaccctga ggtcaagttc     840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagcccctcc cagcccccat cgagaaaacc  1020
atctccaaag ccaagggca gccccgagaa ccacaggtct acaccctgcc ccatcccgg     1080
gaggagatga ccaagaacca ggtcagcctg acctgcctgg tcaaaggctt ctatcccagc   1140
gacatcgccg tggagtggga gagcaatggg cagccggaga caactacaa gaccacgcct    1200
cccgtgctgg actccgacgg ctccttcttc ctctatagca agctcaccgt ggacaagagc   1260
aggtggcagc aggggaacgt cttctcatgc tccgtgatgc atgaggctct gcacaaccac   1320
tacacgcaga gagcctctc cctgtctccg ggtaaaggcg agggggatc cggcggaggg     1380
ggctctgaga tcgtgctgac ccagagcccc ggcaccctga gcctgagccc tggcgagaga  1440
gccaccctga gctgccgggc cagccagtcc atcaccggca gctacctggc ttggtatcag  1500
cagaagcccg gacaggcccc cagactgctg atcaccggca cttccagctg gccaccggc   1560
atccccgaca gattcagcgg cagcggctcc ggcaccgact tcaccctgac catcagcaga  1620
ctggagcccg aggacttcgc cgtgtactac tgccagcagt acagcagcag ccccatccac  1680
ttcggatgcg gcaccaggct ggagatcaag ggcggagggg gctctggggg aggggcagc   1740
ggcggcggag gatctggggg aggggcagc caggtgcagc tggtcgagtc tggcggcgga   1800
gtggtgcagc ccggcagaag cctgagactg agctgcgccg ccagcggctt caccttcacc   1860
aactacggca tgcactgggt ccgccaggcc cctggcaagt gcctggagtg ggtggccgtg   1920
atcagccacg acggcaacaa caagtactac gtggacagcg tgaagggcag attcaccatc   1980
agcagggaca cagcaagaa caccctgtac ctccagatga acagcctgag agccgaggac   2040
accgccgtgt actactgcgc cagagagggc atcgactttt ggagcggcct gaattggttc   2100
gacccctggg gccagggcac cctggtgacc gtgtccagc                          2139
```

<210> SEQ ID NO 3
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30
```

-continued

Glu Met Tyr Trp Val Arg Gln Ala Pro Gly Lys Gly Leu Glu Trp Val
            35                  40                  45

Ser Ser Ile Ser Pro Ser Gly Gly Trp Thr Met Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser
            115                 120

<210> SEQ ID NO 4
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
gaagttcaat tgttagagtc tggtggcggt cttgttcagc ctggtggttc tttacgtctt      60
tcttgcgctg cttccggatt cactttctct tggtacgaga tgtattgggt tcgccaagct     120
cctggtaaag gtttggagtg gtttcttct atctctcctt ctggtggctg gactatgtat      180
gctgactccg ttaaaggtcg cttcactatc tctagagaca actctaagaa tactctctac     240
ttgcagatga acagcttaag ggctgaggac acggccgtgt attactgtgc gaccccttg      300 tatagcagtg acgggctttc ggcggggat atctggggcc aagggacaat ggtcaccgtc      360
tcaagc                                                                366

<210> SEQ ID NO 5
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Thr Asn Tyr
            20                  25                  30

Gly Met His Trp Val Arg Gln Ala Pro Gly Lys Cys Leu Glu Trp Val
            35                  40                  45

Ala Val Ile Ser His Asp Gly Asn Asn Lys Tyr Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Asp Phe Trp Ser Gly Leu Asn Trp Phe Asp Pro
            100                 105                 110

Trp Gly Gln Gly Thr Leu Val Thr Val Ser Ser

<210> SEQ ID NO 6
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

```
caggtgcagc tggtcgagtc tggcggcgga gtggtgcagc ccggcagaag cctgagactg     60
agctgcgccg ccagcggctt caccttcacc aactacggca tgcactgggt ccgccaggcc    120
cctggcaagt gcctggagtg ggtggccgtg atcagccacg acggcaacaa caagtactac    180
gtggacagcg tgaagggcag attcaccatc agcagggaca cagcaagaa caccctgtac     240
ctccagatga acagcctgag agccgaggac accgccgtgt actactgcgc cagagagggc    300
atcgactttt ggagcggcct gaattggttc gaccccctggg gccagggcac cctggtgacc    360
gtgtccagc                                                            369
```

<210> SEQ ID NO 7
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Arg Thr Pro
                85                  90                  95

Ser Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
gagatcgtgc tgacccagtc tccagccacc ctctctttgt ctccagggga aagagccacc    60
ctctcctgca gggccagtca gagtgttcac agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagttta ctactgtcaa cagagttacc gcaccccttc cttcggccaa   300
gggacacgac tggagattaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642

<210> SEQ ID NO 9
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Arg Thr Pro
                85                  90                  95

Ser Phe Gly Gln Gly Thr Arg Leu Glu Ile Lys
            100                 105

<210> SEQ ID NO 10
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10

```
gagatcgtgc tgacccagtc tccagccacc ctctctttgt ctccagggga aagagccacc    60
ctctcctgca gggccagtca gagtgttcac agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagttta ctactgtcaa cagagttacc gcaccccttc cttcggccaa   300
gggacacgac tggagattaa a                                              321
```

<210> SEQ ID NO 11
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Thr Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Cys Gly Thr Arg Leu Glu Ile Lys
            100                 105
```

<210> SEQ ID NO 12
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

```
gagatcgtgc tgacccagag ccccggcacc ctgagcctga gccctggcga gagagccacc    60
ctgagctgcc gggccagcca gtccatcacc ggcagctacc tggcttggta tcagcagaag   120
cccggacagg cccccagact gctgatcacc ggcgcttcca gctgggccac cggcatcccc   180
gacagattca gcggcagcgg ctccggcacc gacttcaccc tgaccatcag cagactggag   240
cccgaggact cgccgtgta ctactgccag cagtacagca gcagccccat caccttcgga   300
tgcggcacca ggctggagat caag                                          324
```

<210> SEQ ID NO 13
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 13

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Thr Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Cys Gly Thr Arg Leu Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Val Val Gln Pro Gly Arg
    130                 135                 140

Ser Leu Arg Leu Ser Cys Ala Ala Ser Gly Phe Thr Phe Thr Asn Tyr
145                 150                 155                 160

Gly Met His Trp Val Arg Gln Ala Pro Gly Lys Cys Leu Glu Trp Val
                165                 170                 175

Ala Val Ile Ser His Asp Gly Asn Asn Lys Tyr Tyr Val Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Glu Gly Ile Asp Phe Trp Ser Gly Leu Asn Trp Phe Asp Pro
225                 230                 235                 240

Trp Gly Gln Gly Thr Leu Val Thr Val Ser Ser
                245                 250
```

<210> SEQ ID NO 14
<211> LENGTH: 753
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 14

```
gagatcgtgc tgacccagag ccccggcacc ctgagcctga gccctggcga gagagccacc      60
ctgagctgcc gggccagcca gtccatcacc ggcagctacc tggcttggta tcagcagaag     120
cccggacagg cccccagact gctgatcacc ggcgcttcca gctgggccac cggcatcccc     180
gacagattca gcggcagcgg ctccggcacc gacttcaccc tgaccatcag cagactggag     240
cccgaggact tcgccgtgta ctactgccag cagtacagca gcagccccat caccttcgga     300
tgcggcacca ggctggagat caagggcgga ggggctctg ggagggggg cagcggcggc      360 ggaggatctg ggggagggg cagccaggtg cagctggtcg agtctggcgg cggagtggtg     420
```

```
cagcccggca gaagcctgag actgagctgc gccgccagcg gcttcacctt caccaactac    480
ggcatgcact gggtccgcca ggcccctggc aagtgcctgg agtgggtggc cgtgatcagc    540
cacgacggca acaacaagta ctacgtggac agcgtgaagg gcagattcac catcagcagg    600
gacaacagca gaacacccct gtacctccag atgaacagcc tgagagccga ggacaccgcc    660
gtgtactact gcgccagaga gggcatcgac ttttggagcg gcctgaattg gttcgacccc    720
tggggccagg gcaccctggt gaccgtgtcc agc                                 753
```

```
<210> SEQ ID NO 15
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Gly Gly Gly Ser Gly Gly Gly Gly Ser Gly Gly Gly Gly Ser Gly
1               5                   10                  15

Gly Gly Gly Ser
            20

<210> SEQ ID NO 16
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Gly Gly Gly Ser Gly Gly Gly Gly Ser
1               5                   10

<210> SEQ ID NO 17
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Trp Tyr Glu Met Tyr
1               5

<210> SEQ ID NO 18
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ser Ile Ser Pro Ser Gly Gly Trp Thr Met Tyr Ala Asp Ser Val Lys
1               5                   10                  15

Gly

<210> SEQ ID NO 19
```

```
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Pro Leu Tyr Ser Ser Asp Gly Leu Ser Ala Gly Asp Ile
1               5                   10

<210> SEQ ID NO 20
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Arg Ala Ser Gln Ser Val His Ser Ser Tyr Leu Ala
1               5                   10

<210> SEQ ID NO 21
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gly Ala Ser Ser Arg Ala Thr
1               5

<210> SEQ ID NO 22
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gln Gln Ser Tyr Arg Thr Pro Ser
1               5

<210> SEQ ID NO 23
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gly Phe Thr Phe Thr Asn Tyr Gly Met His
1               5                   10

<210> SEQ ID NO 24
<211> LENGTH: 17
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 24

Val Ile Ser His Asp Gly Asn Asn Lys Tyr Tyr Val Asp Ser Val Lys
1               5                   10                  15

Gly

<210> SEQ ID NO 25
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Glu Gly Ile Asp Phe Trp Ser Gly Leu Asn Trp Phe Asp Pro
1               5                   10

<210> SEQ ID NO 26
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Arg Ala Ser Gln Ser Ile Thr Gly Ser Tyr Leu Ala
1               5                   10

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Ala Ser Ser Trp Ala Thr
1               5

<210> SEQ ID NO 28
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gln Gln Tyr Ser Ser Ser Pro Ile Thr
1               5

<210> SEQ ID NO 29
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
```

<400> SEQUENCE: 29

```
gagatcgtgc tgacccagtc tccagccacc ctctctttgt ctccagggga aagagccacc      60
ctctcctgca gggccagtca gagtgttcac agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagttta ctactgtcaa cagagttacc gcacccttc cttcggccaa      300 gggacacgac tggagattaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

<210> SEQ ID NO 30
<211> LENGTH: 2139
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30

```
gaagttcaat tgttagagtc tggtggcggt cttgttcagc ctggtggttc tttacgtctt      60
tcttgcgctg cttccggatt cactttctct tggtacgaga tgtattgggt tcgccaagct     120
cctggtaaag gtttggagtg gtttcttct atctctcctt ctggtggctg gactatgtat      180
gctgactccg ttaaaggtcg cttcactatc tctagagaca actctaagaa tactctctac     240
ttgcagatga acagcttaag ggctgaggac acggccgtgt attactgtgc gaccccttg      300 tatagcagtg acgggctttc ggcggggat atctgggggcc aagggacaat ggtcaccgtc      360
tcaagcgcgt cgaccaaggg cccatccgtc ttccccctgg cacctcctc caagagcacc      420 tctgggggca gcggccct gggctgcctg gtcaaggact acttccccga accggtgacg      480
gtgtcctgga actcaggcgc tctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaactcctg     720
gggggaccgt cagtcttcct cttccccca aaacccaagg acaccctcat gatctcccgg     780 accccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagcccccat cgagaaaacc    1020
atctccaaag ccaaagggca gccccgagaa ccacaggtct acaccctgcc cccatcccgg    1080
gaggagatga ccaagaacca ggtcagcctg acctgcctgg tcaaaggctt ctatcccagc    1140
gacatcgccg tggagtggga gagcaatggg cagccggaga caactacaa gaccacgcct    1200 cccgtgctgg actccgacgg ctccttcttc ctctatagca agctcaccgt ggacaagagc    1260
```

-continued

```
aggtggcagc aggggaacgt cttctcatgc tccgtgatgc atgaggctct gcacaaccac    1320
tacacgcaga agagcctctc cctgtctccg ggtaaaggcg gagggggatc cggcggaggg    1380
ggctctgaga tcgtgctgac ccagagcccc ggcaccctga gcctgagccc tggcgagaga    1440
gccaccctga gctgccgggc cagccagtcc atcaccggca gctacctggc ttggtatcag    1500
cagaagcccg acaggcccca gactgctgat caccggcgc ttccagctg gccaccggc      1560 atccccgaca gattcagcgg cagcggctcc ggcaccgact tcaccctgac catcagcaga    1620
ctggagcccg aggacttcgc cgtgtactac tgccagcagt acagcagcag ccccatcacc    1680
ttcggatgcg gcaccaggct ggagatcaag ggcggagggg gctctggggg agggggcagc    1740
ggcggcggag gatctggggg aggggggcagc caggtgcagc tggtcgagtc tggcggcgga    1800
gtggtgcagc ccggcagaag cctgagactg agctgcgccg ccagcggctt caccttcacc    1860
aactacggca tgcactgggt ccgccaggcc cctggcaagt gcctggagtg ggtggccgtg    1920
atcagccacg acggcaacaa caagtactac gtggacagcg tgaagggcag attcaccatc    1980
agcagggaca cagcaagaa caccctgtac ctccagatga acagcctgag agccgaggac    2040
accgccgtgt actactgcgc cagagagggc atcgactttt ggagcggcct gaattggttc    2100
gaccctgggg gccagggcac cctggtgacc gtgtccagc                          2139
```

```
<210> SEQ ID NO 31
<211> LENGTH: 713
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
             20                  25                  30

Glu Met Tyr Trp Val Arg Gln Ala Pro Gly Lys Gly Leu Glu Trp Val
         35                  40                  45

Ser Ser Ile Ser Pro Ser Gly Gly Trp Thr Met Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

-continued

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
    435                 440                 445

Ser Pro Gly Lys Gly Gly Gly Ser Gly Gly Gly Gly Ser Glu Ile
450                 455                 460

Val Leu Thr Gln Ser Pro Gly Thr Leu Ser Leu Ser Pro Gly Glu Arg
465                 470                 475                 480

Ala Thr Leu Ser Cys Arg Ala Ser Gln Ser Ile Thr Gly Ser Tyr Leu
                485                 490                 495

Ala Trp Tyr Gln Gln Lys Pro Gly Gln Ala Pro Arg Leu Leu Ile Thr
            500                 505                 510

Gly Ala Ser Ser Trp Ala Thr Gly Ile Pro Asp Arg Phe Ser Gly Ser
    515                 520                 525

Gly Ser Gly Thr Asp Phe Thr Leu Thr Ile Ser Arg Leu Glu Pro Glu
530                 535                 540

Asp Phe Ala Val Tyr Tyr Cys Gln Gln Tyr Ser Ser Ser Pro Ile Thr
545                 550                 555                 560

Phe Gly Cys Gly Thr Arg Leu Glu Ile Lys Gly Gly Gly Gly Ser Gly
                565                 570                 575

Gly Gly Gly Ser Gly Gly Gly Gly Ser Gly Gly Gly Gly Ser Gln Val
            580                 585                 590

Gln Leu Val Glu Ser Gly Gly Val Val Gln Pro Gly Arg Ser Leu
    595                 600                 605

Arg Leu Ser Cys Ala Ala Ser Gly Phe Thr Phe Thr Asn Tyr Gly Met

```
                610                 615                 620
His Trp Val Arg Gln Ala Pro Gly Lys Cys Leu Glu Trp Val Ala Val
625                 630                 635                 640

Ile Ser His Asp Gly Asn Asn Lys Tyr Tyr Val Asp Ser Val Lys Gly
                645                 650                 655

Arg Phe Thr Ile Ser Arg Asp Asn Ser Lys Asn Thr Leu Tyr Leu Gln
                660                 665                 670

Met Asn Ser Leu Arg Ala Glu Asp Thr Ala Val Tyr Tyr Cys Ala Arg
            675                 680                 685

Glu Gly Ile Asp Phe Trp Ser Gly Leu Asn Trp Phe Asp Pro Trp Gly
            690                 695                 700

Gln Gly Thr Leu Val Thr Val Ser Ser
705                 710
```

<210> SEQ ID NO 32
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 32

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

NUCLEIC ACIDS ENCODING BISPECIFIC ANTI-VEGF AND ANTI-ANG2 ANTIBODIES AND USES THEREOF

CROSS-REFERENCE TO RELATED APPLICATIONS

This application is a divisional of U.S. patent application Ser. No. 16/327,207, filed on Feb. 21, 2019, which is a U.S. National Stage Application under 35 U.S.C. § 371 of International Application No. PCT/EP2017/071104, filed on Aug. 22, 2017, which claims the benefit under 35 U.S.C. § 119(e) of the U.S. Provisional Application No. 62/378,388, filed Aug. 23, 2016. Each of the above listed applications is incorporated by reference herein in its entirety for all purposes.

REFERENCE TO THE SEQUENCE LISTING

This application incorporates by reference a Sequence Listing submitted with this application as text file entitled ANGVE-105-WO-PCT_SL, created on Jan. 9, 2019, and having a size of 40435 bytes.

FIELD OF THE INVENTION

The invention relates to bispecific antibodies having activity against a vascular endothelial growth factor (VEGF) and an angiopoietin (ANG), and uses of such antibodies.

BACKGROUND TO THE INVENTION

Angiogenesis, the formation of new blood vessels from existing vasculature, is a complex biological process required for the formation and physiological functions of virtually all the organs. It is an essential element of embryogenesis, normal physiological growth, repair and pathological processes such as tumour expansion. Normally, angiogenesis is tightly regulated by the local balance of angiogenic and angiostatic factors in a multi-step process involving vessel sprouting, branching and tubule formation by endothelial cells (involving processes such as activation of endothelial cells (ECs), vessel destabilisation, synthesis and release of degradative enzymes, EC migration, EC proliferation, EC organization and differentiation and vessel maturation).

In the adult, physiological angiogenesis is largely confined to wound healing and several components of female reproductive function and embryonic development. In disease-related angiogenesis which includes any abnormal, undesirable or pathological angiogenesis, the local balance between angiogenic and angiostatic factors is dysregulated leading to inappropriate and/or structurally abnormal blood vessel formation. Pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacology. Science. 16: 57-66; Folkman, 1995, Nature Medicine 1: 27-31). In cancer, growth of primary and secondary tumours beyond 1-2 $mm^3$ requires angiogenesis (Folkman, J. New England Journal of Medicine 1995; 33, 1757-1763).

VEGF is a potent and ubiquitous vascular growth factor. Prior to identification of the role of VEGF as a secreted mitogen for endothelial cells, it was identified as a vascular permeability factor, highlighting VEGF's ability to control many distinct aspects of endothelial cell behaviour, including proliferation, migration, specialization and survival (Ruhrberg, 2003 BioEssays 25:1052-1060). VEGF family members include VEGF-A, VEGF-B, VEGF-C, VEGF-D, VEGF-E, placental growth factor (PlGF) and endocrine gland-derived VEGF (EG-VEGF). Active forms of VEGF are synthesised either as homodimers or heterodimers with other VEGF family members. VEGF-A exists in six isoforms generated by alternative splicing: VEGF121, VEGF145, VEGF165, VEGF183, VEGF189 and VEGF206. These isoforms differ primarily in their bioavailability, with VEGF165 being the predominant isoform (Podar, et al. 2005 Blood 105(4):1383-1395). The regulation of splicing during embryogenesis to produce stage- and tissue-specific ratios of the various isoforms creates rich potential for distinct and context dependent behaviour of endothelial cells in response to VEGF.

VEGF is believed to be an important stimulator of both normal and disease-related angiogenesis (Jakeman, et al. 1993 Endocrinology: 133,848-859; Kolch, et al. 1995 Breast Cancer Research and Treatment: 36,139-155) and vascular permeability (Connolly, et al. 1989 J. Biol. Chem: 264, 20017-20024). Antagonism of VEGF action by sequestration of VEGF with antibodies can result in a reduction in tumor growth (Kim, et al. 1993 Nature: 362, 841-844). Heterozygous disruption of the VEGF gene resulted in fatal deficiencies in vascularisation (Carmeliet, et al. 1996 Nature 380:435-439; Ferrara, et al. 1996 Nature 380:439-442).

In addition to the VEGF family, the angiopoietins are thought to be involved in vascular development and postnatal angiogenesis. The angiopoietins include a naturally occurring agonist, angiopoietin-1 (ANG-1), as well as a naturally occurring antagonist, angiopoietin-2 (ANG-2). The role of ANG-1 is thought to be conserved in the adult, where it is expressed widely and constitutively (Hanahan, *Science,* 277:48-50 (1997); Zagzag, et al., *Exp Neurology,* 159:391-400 (1999)). In contrast, ANG-2 expression is primarily limited to sites of vascular remodeling where it is thought to block the constitutive stabilizing or maturing function of ANG-1, allowing vessels to revert to, and remain in, a plastic state which may be more responsive to sprouting signals (Hanahan, 1997; Holash et al., *Oncogene* 18:5356-62 (1999); Maisonpierre, 1997). Studies of ANG-2 expression in disease-related angiogenesis have found many tumor types to show vascular ANG-2 expression (Maisonpierre et al., *Science* 277:55-60 (1997)). Functional studies suggest ANG-2 is involved in tumor angiogenesis and associate ANG-2 overexpression with increased tumor growth in a mouse xenograft model (Ahmad, et al., *Cancer Res.,* 61:1255-1259 (2001)). Other studies have associated ANG-2 overexpression with tumor hypervascularity (Etoh, et al., *Cancer Res.* 61:2145-53 (2001); Tanaka et al., *Cancer Res.* 62:7124-29 (2002)).

Using homology-based cloning approaches, Valenzuela et al. (*Proc Natl Acad Sci U S A.* 1999 Mar. 2; 96(5):1904-9) identified 2 novel angiopoietins: angiopoietin-3 (ANG-3) in mouse, and angiopoietin-4 (ANG-4) in human. Although ANG-3 and ANG-4 are more structurally diverged from each other than are the mouse and human versions of ANG-1 and ANG-2, they appear to represent the mouse and human counterparts of the same gene locus. Very little is known about the biology of these members of the angiopoietin family. For example, ANG-4 is expressed at high levels only in the lung (Tsigkos, et al., Expert Opin. Investig. Drugs 12(6): 933-941 (2003); Valenzuela, et al., Proc. Natl. Acad. Sci. 96:1904-1909 (1999)). ANG-4 expression levels are known to increase in response to hypoxia, and endothelial cell growth factors lead to increasing levels of ANG-4 expression in a glioblastoma cell line and endothelial cells.

However, the mechanism of expression regulation, and the resulting effect on physiological and disease-related angiogenesis are unknown (Lee, et al., FASEB J. 18: 1200-1208 (2004).

The angiopoietins were first discovered as ligands for the Tie receptor tyrosine kinase family that is selectively expressed within the vascular endothelium (Yancopoulos et al., Nature 407:242-48 (2000). ANG-1, ANG-2, ANG-3 and ANG-4 bind primarily to the Tie-2 receptor and so are also known as Tie-2 ligands. Binding of ANG-1 to Tie-2 induces tyrosine phosphorylation of the receptor via autophosphorylation and subsequently activation of its signalling pathways via signal transduction (Maisonpierre, P. et al. 1997 Science: 277, 55-60). ANG-2 is a naturally occurring antagonist for ANG-1 acting through competitive inhibition of ANG-1-induced kinase activation of the Tie-2 receptor (Hanahan, 1997; Davis et al., Cell 87:1161-69 (1996); Maisonpierre et al., Science 277:55-60 (1997)).

Knock-out mouse studies of Tie-2 and ANG-1 show similar phenotypes and suggest that ANG-1 stimulated Tie-2 phosphorylation mediates remodeling and stabilization of developing vessel, promoting blood vessel maturation during angiogenesis and maintenance of endothelial cell-support cell adhesion (Dumont et al., Genes & Development, 8:1897-1909 (1994); Sato, Nature, 376:70-74 (1995); (Thurston, G. et al., 2000 Nature Medicine: 6, 460-463)).

In recent years ANG-1, ANG-2 and/or Tie-2 have been proposed as possible anti-cancer therapeutic targets (see, for example, U.S. Pat. Nos. 6,166,185, 5,650,490 and 5,814,464 each disclose anti-Tie-2 ligand and receptor antibodies). Studies using soluble Tie-2 have been reported to decrease the number and size of tumors in rodents. Also, some groups have reported the use of antibodies that bind to ANG-2 (see, for example, U.S. Pat. No. 6,166,185 and U.S. Patent Application Publication No. 2003/0124129) and antibodies that bind to VEGF-A (see, for example, U.S. Pat. No. 8,216,571). Additionally, there are examples of targeting VEGF-A and ANG-2 (see, for example, WO200197850, WO2007089445, and U.S. Pat. No. 8,268,314). However, there is an unmet need is the medical arts for a bispecific antibody targeting VEGF-A and ANG-2 that is more tolerable or effective. More particularly, there is an unmet need related to improving the safety at least as it relates to toxicity associated with targeting VEGF-A (e.g., thromboembolic events, renal toxicity, etc.). To this end, the bispecific antibodies targeting VEGF-A and ANG-2 disclosed herein are effective at reducing vascular dysregulation and tumor growth with a decrease in toxicity related to, for example, thromboembolic events and/or renal toxicity.

SUMMARY OF THE INVENTION

The invention relates to bispecific antibodies that bind to VEGF and ANG. The invention further relates to bispecific antibodies that bind to VEGF and ANG, and reduce the activity of at least one biological activity of VEGF and ANG. The invention even further relates to providing bispecific antibodies to a subject in need thereof that bind to VEGF and ANG, and reduce tumor growth and/or reduce tumor volume.

BRIEF DESCRIPTION OF THE FIGURES

FIG. 1 depicts a schematic of the general structural format of five different bispecific antibody (BiS) backbones, BiS1, BiS2, BiS3, BiS4, and BiS5. The scFv is depicted in dark grey and the IgG Fv is depicted in light grey.

FIG. 3 depicts the DNA and protein sequences for the light chain of the bispecific antibody BiS3Ab-VEGF H1RK-ANG-2.

FIG. 4 depicts the DNA sequence of the heavy chain of the bispecific antibody BiS3Ab-VEGF H1RK-ANG-2.

FIG. 5 depicts the protein sequence of the heavy chain of the bispecific antibody BiS3Ab-VEGF H1RK-ANG-2.

FIG. 6 depicts representative data for an elution profile for the bispecific antibody BiSAb-VEGF H1RK-ANG-2.

FIG. 19 depicts representative data showing reduction of the vessel branching in the presence of BiSAb-VEGF H1RK-ANG-2. 20× magnification.

DETAILED DESCRIPTION

Definitions

Figure 2:
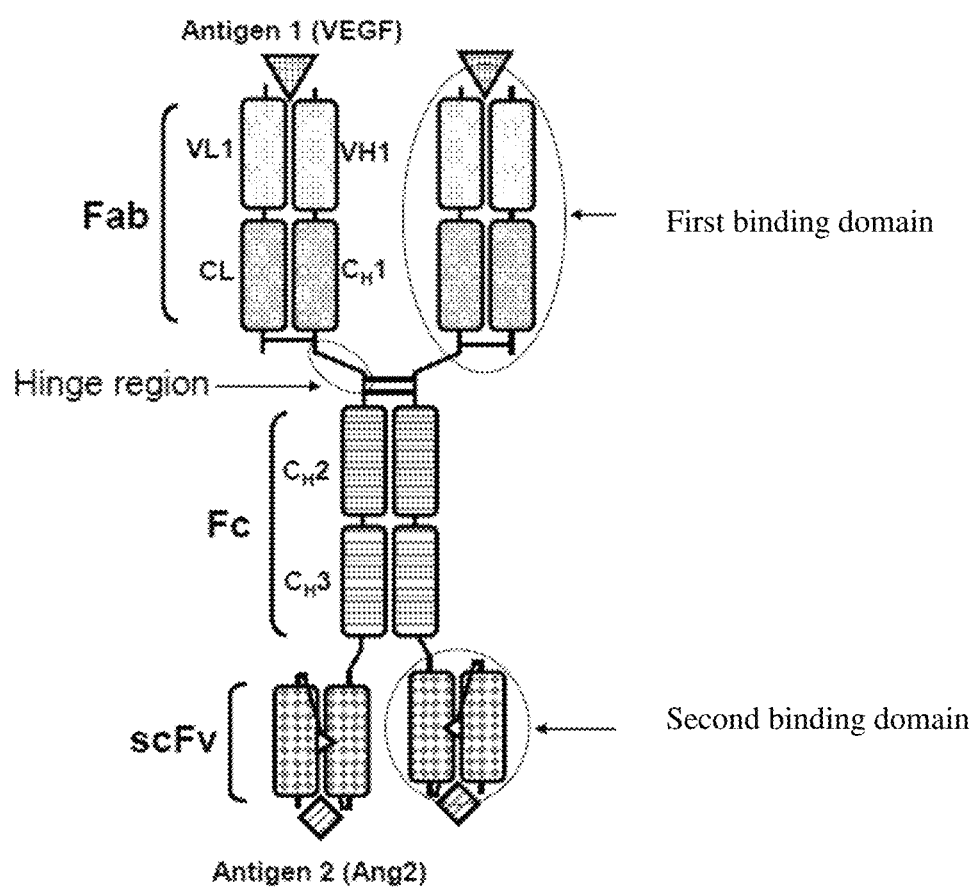
FIG. 2 depicts a schematic representation of the bispecific antibody BiS3Ab-VEGF H1RK-ANG-2.

Before describing the present invention in detail, it is to be understood that this invention is not limited to specific compositions or process steps, as such can vary. As used in this specification and the appended claims, the singular forms "a," "an" and "the" include plural referents unless the context clearly dictates otherwise. The terms "a" (or "an"), as well as the terms "one or more," and "at least one" can be used interchangeably herein. Further it is understood that wherever aspects are described herein with the language "comprising," otherwise analogous aspects described in terms of "consisting of" and/or "consisting essentially of" are also provided.

Complementarity determining regions (CDRs) are responsible for antibody binding to its antigen. CDRs are determined by a number of methods in the art (including Kabat (Kabat et al., Sequences of Proteins of Immunological Interest, 5th Ed. Public Health Service, National Institutes of Health, Bethesda, Md. (1991)); Chothia (Chothia and Lesk, J. Mol. Biol. 196:901-917 (1987)); IMGT (ImMunoGeneTics) (Lefranc, M. P. et al., Dev. Comp. Immunol. 27: 55-77 (2003)); and other methods). Although specific CDR sequences are mentioned and claimed herein, the invention also encompasses CDR sequences defined by any method known in the art.

As use herein, the term "subject" refers to any member of the subphylum *cordata*, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like are also non-limiting examples.

Bispecific Antibodies

Suitable bispecific antibodies of the invention can be or are derived from any isotype (e.g., IgG, IgE, IgM, IgD, IgA and IgY), sub-isotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Such antibodies can include light chains classified as either lambda chains or kappa chains based on the amino acid sequence of the light chain constant region. FIG. 1 shows a schematic of the orientation of five different bispecific backbones (BiS) (see, for example, PCT Patent Application Nos. PCT/US2016/035026 and PCT/US2015/025232). Specific linkers within the scFv and linkers linking the scFv to a specified portion of bispecific antibodies of the invention (e.g., GGGGSGGGGSGGGGSGGGGS (SEQ ID NO: 15)) are described. However, any suitable linker within the scFv or linking the scFv to any specified portion of bispecific antibodies of the invention may be used (see, for example, PCT Patent Application Nos. PCT/US2016/035026 and PCT/US2015/025232).

Production of Binding Molecules

Recombinant DNA methods for producing and screening for bispecific antibodies described herein are known in the art (e.g. U.S. Pat. No. 4,816,567). DNA encoding the bispecific antibodies, for example, DNA encoding a VH domain, a VL domain, a single chain variable fragment (scFv), or combinations thereof can be inserted into a suitable expression vector, which can then be transfected into a suitable host cell, such as *E. coli* cells, simian COS cells, Chinese Hamster Ovary (CHO) cells, or myeloma cells that do not otherwise produce an antibody, to obtain the bispecific antibodies of the invention.

Suitable expression vectors are known in the art. An expression vector can contain a polynucleotide that encodes a bispecific antibody linked to a promoter. Such vectors may include the nucleotide sequence encoding the constant region of the antibody molecule (see, e.g., U.S. Pat. Nos. 5,981,216; 5,591,639; 5,658,759 and 5,122,464) and the variable domain of the antibody may be cloned into such a vector for expression of the entire heavy chain (including the scFv portion), the entire light chain, or both the entire heavy and light chains. The expression vector can be transferred to a host cell by conventional techniques and the transfected cells can be cultured by conventional techniques to produce the bispecific antibodies.

Mammalian cell lines suitable as hosts for expression of recombinant antibodies are known in the art and include many immortalized cell lines available from the American Type Culture Collection, including but not limit to CHO cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the bispecific antibodies. To this end, eukaryotic host cells which possess the cellular machinery for proper processing of the primary transcript, glycosylation, and phosphorylation of the gene product may be used. Such mammalian host cells include CHO, VERY, BHK, Hela, COS, MDCK, 293, 3T3, W138, BT483, Hs578T, HTB2, BT2O and T47D, NSO (a murine myeloma cell line that does not endogenously produce any functional immunoglobulin chains), SP20, CRL7O3O and HsS78Bst cells. Human cell lines developed by immortalizing human lymphocytes can be used to recombinantly produce monoclonal antibodies. The human cell line PER.C6® (Crucell, Netherlands) can be used to recombinantly produce monoclonal antibodies. Additional cell lines which may be used as hosts for expression of recombinant antibodies include insect cells (e.g. Sf21/Sf9, *Trichoplusia ni* Bti-Tn5b1-4), or yeast cells (e.g. *S. cerevisiae, Pichia*, U.S. Pat. No. 7,326,681; etc.), plants cells (US20080066200), or chicken cells (WO2008142124).

Bispecific antibodies can be stably expressed in a cell line using methods known in the art. Stable expression can be used for long-term, high-yield production of recombinant proteins. For stable expression, host cells can be transformed with an appropriately engineered vector that includes expression control elements (e.g., promoter, enhancer, transcription terminators, polyadenylation sites, etc.), and a selectable marker gene. Following the introduction of the foreign DNA, cells are allowed to grow for 1-2 days in an enriched media, and are then switched to a selective media. The selectable marker in the recombinant plasmid confers resistance to the selection and allows cells that have stably integrated the plasmid into their chromosomes to grow and form foci which in turn can be cloned and expanded into cell lines. Methods for producing stable cell lines with a high yield are known in the art and reagents are generally available commercially. Transient expression can also be carried out by using methods known in the art. Transient transfection is a process in which the nucleic acid introduced into a cell does not integrate into the genome or chromosomal DNA of that cell and is maintained as an extrachromosomal element in the cell (e.g., as an episome).

A cell line expressing a bispecific antibody, either stable or transiently transfected, can be maintained in cell culture medium and conditions known in the art resulting in the expression and production of the bispecific antibodies. Cell culture media can be based on commercially available media formulations, including, for example, DMEM or Ham's F12. In addition, the cell culture media can be modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be optimized for a specific cell culture use, including cell culture growth medium which is formulated to promote cellular growth or cell culture production medium which is formulated to promote recombinant protein production. The terms nutrient, ingredient, and component are used interchangeably herein to refer to the constituents that make up a cell culture medium. Cell lines can be maintained using a fed batch method. As used herein, "fed batch method," refers to a method by which a cell culture is supplied with additional nutrients after first being incubated with a basal medium. For example, a fed batch method may include adding supplemental media according to a determined feeding schedule within a given time period. Thus, a "fed batch cell culture" refers to a cell culture wherein the cells, typically mammalian, and culture medium are supplied to the culturing vessel initially and additional culture nutrients are fed, continuously or in discrete increments, to the culture during culturing, with or without periodic cell and/or product harvest before termination of culture.

Cell culture media and the nutrients contained therein are known in the art. Cell culture medium may include a basal medium and at least one hydrolysate, e.g., soy-based hydrolysate, a yeast-based hydrolysate, or a combination of the two types of hydrolysates resulting in a modified basal medium. The additional nutrients may include only a basal medium, such as a concentrated basal medium, or may include only hydrolysates, or concentrated hydrolysates. Suitable basal media include Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (see, e.g., CHO protein free medium (Sigma) or EX-CELL™ 325 PF CHO Serum-Free Medium for CHO Cells Protein-Free (SAFC Bioscience), and Iscove's Modified Dulbecco's Medium. Other examples of basal media which may be used include BME Basal Medium (Gibco-Invitrogen; see also Eagle, H (1965) Proc. Soc. Exp. Biol. Med. 89, 36); Dulbecco's Modified Eagle Medium (DMEM, powder) (Gibco-Invitrogen (#31600); see also Dulbecco and Freeman (1959) Virology. 8:396; Smith et al. (1960) Virology. 12:185. Tissue Culture Standards Committee, In Vitro 6:2, 93); CMRL 1066 Medium (Gibco-Invitrogen (#11530); see also Parker et al. (1957) Special Publications, N.Y. Academy of Sciences, 5:303).

The basal medium may be serum-free, meaning that the medium contains no serum (e.g., fetal bovine serum (FBS), horse serum, goat serum, or any other animal-derived serum known to one skilled in the art) or animal protein free media or chemically defined media.

The basal medium may be modified in order to remove certain non-nutritional components found in standard basal medium, such as various inorganic and organic buffers, surfactant(s), and sodium chloride. Removing such components from basal cell medium allows an increased concentration of the remaining nutritional components, and may improve overall cell growth and protein expression. In addition, omitted components may be added back into the cell culture medium containing the modified basal cell medium according to the requirements of the cell culture conditions. The cell culture medium may contain a modified basal cell medium, and at least one of the following nutrients, an iron source, a recombinant growth factor; a buffer; a surfactant; an osmolarity regulator; an energy source; and non-animal hydrolysates. In addition, the modified basal cell medium may optionally contain amino acids, vitamins, or a combination of both amino acids and vitamins. A modified basal medium may further contain glutamine, e.g, L-glutamine, and/or methotrexate.

Purification and Isolation

Once a bispecific antibody has been produced, it may be purified by methods known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the bispecific antibodies of the invention may be fused to heterologous polypeptide sequences (referred to herein as "tags") to facilitate purification.

Uses

Bispecific antibodies of the invention can be used in a number of ways. For example, bispecific antibodies of the invention can be used to bind to VEGF, ANG, or any combination of these proteins and thereby reduce at least one biological activity of VEGF, ANG, or any combination of these activities. More particularly, the bispecific antibodies of the invention can be used to bind to VEGF-165, ANG-2, or any combination of these proteins and thereby reduce at least one biological activity of VEGF-165, ANG-2, or any combination of these activities, which may include a reduction in activation or phosphorylation of their respective receptors and/or a reduction in angiogenesis in connection with cellular dysregulation.

Exemplary Embodiments

An embodiment of the invention relates to a bispecific antibody comprising a first binding domain comprising heavy chain complementarity determining regions 1-3 (i.e., HCDR1, HCDR2, and HCDR3) and light chain complementarity determining regions 1-3 (i.e., LCDR1, LCDR2, and LCDR3) of a bispecific antibody described herein, and a second binding domain comprising an HCDR1, HCDR2, and HCDR3 and an LCDR1, LCDR2, and LCDR3 of a bispecific antibody described herein, wherein the first binding domain binds to VEGF-A and the second binding domain binds to ANG-2. In a further embodiment the bispecific antibody is BiS3Ab-VEGF H1RK-ANG-2.

Another embodiment relates to a bispecific antibody comprising a first binding domain comprising an HCDR1, HCDR2, and HCDR3 and an LCDR1, LCDR2, and LCDR3 of a bispecific antibody described herein, and a second binding domain comprising an HCDR1, HCDR2, and HCDR3 and an LCDR1, LCDR2, and LCDR3 of a bispecific antibody described herein, wherein the first binding domain binds to VEGF-A and the second binding domain binds to ANG-2 and wherein the bispecific antibody binds VEGF165. In a further embodiment the bispecific antibody is BiS3Ab-VEGF H1RK-ANG-2.

Another embodiment relates to a bispecific antibody comprising a first binding domain comprising an HCDR1, HCDR2, and HCDR3 and an LCDR1, LCDR2, and LCDR3 of a bispecific antibody described herein and a second binding domain comprising an HCDR1, HCDR2, and HCDR3 and an LCDR1, LCDR2, and LCDR3 of a bispecific antibody described herein, wherein the first binding domain binds to VEGF-A and the second binding domain binds to ANG-2 and wherein the bispecific antibody binds VEGF165 with greater affinity compared to VEGF121. In a further embodiment the bispecific antibody is BiS3Ab-VEGF H1RK-ANG-2.

Another embodiment relates to a bispecific antibody comprising a first binding domain comprising an HCDR1, HCDR2, and HCDR3 and an LCDR1, LCDR2, and LCDR3 of a bispecific antibody described herein and a second binding domain comprising an HCDR1, HCDR2, and HCDR3 and an LCDR1, LCDR2, and LCDR3 of a bispecific antibody described herein, wherein the first binding domain binds to VEGF-A and the second binding domain binds to ANG-2 and wherein the bispecific antibody binds VEGF165 with greater affinity compared to VEGF189. In a further embodiment the bispecific antibody is BiS3Ab-VEGF H1RK-ANG-2.

Another embodiment relates to a bispecific antibody comprising a first binding domain comprising an HCDR1, HCDR2, and HCDR3 and an LCDR1, LCDR2, and LCDR3 of a bispecific antibody described herein and a second binding domain comprising an HCDR1, HCDR2, and HCDR3 and an LCDR1, LCDR2, and LCDR3 of a bispecific antibody described herein, wherein the first binding domain binds to VEGF-A and the second binding domain binds to ANG-2 and wherein the bispecific antibody binds VEGF165 with greater affinity compared to VEGF121 and VEGF189. In a further embodiment the bispecific antibody is BiS3Ab-VEGF H1RK-ANG-2.

Another embodiment relates to a bispecific antibody comprising a first binding domain comprising an HCDR1, HCDR2, and HCDR3 and an LCDR1, LCDR2, and LCDR3 of a bispecific antibody described herein and a second binding domain comprising an HCDR1, HCDR2, and HCDR3 and an LCDR1, LCDR2, and LCDR3 of a bispecific antibody described herein, wherein the first binding domain binds to VEGF-A and the second binding domain binds to ANG-2 and wherein the bispecific antibody reduces human VEGFR2 phosphorylation, murine VEGFR2 phosphorylation, or both human and murine VEGFR2 phosphorylation. In a further embodiment the bispecific antibody is BiS3Ab-VEGF H1RK-ANG-2.

Another embodiment relates to a bispecific antibody comprising a first binding domain comprising an HCDR1, HCDR2, and HCDR3 and an LCDR1, LCDR2, and LCDR3 of a bispecific antibody described herein and a second binding domain comprising an HCDR1, HCDR2, and HCDR3 and an LCDR1, LCDR2, and LCDR3 of a bispecific antibody described herein, wherein the first binding domain binds to VEGF-A and the second binding domain binds to ANG-2 and wherein the bispecific antibody reduces human Tie2 receptor phosphorylation. In a further embodiment the bispecific antibody is BiS3Ab-VEGF H1RK-ANG-2.

Another embodiment relates to a bispecific antibody comprising a first binding domain comprising an HCDR1, HCDR2, and HCDR3 and an LCDR1, LCDR2, and LCDR3 of a bispecific antibody described herein and a second binding domain comprising an HCDR1, HCDR2, and HCDR3 and an LCDR1, LCDR2, and LCDR3 of a bispecific antibody described herein, wherein the first binding domain binds to VEGF-A and the second binding domain binds to ANG-2 and wherein the bispecific antibody reduces angiogenesis.

Another embodiment relates to a bispecific antibody comprising a first binding domain comprising an HCDR1, HCDR2, and HCDR3 and an LCDR1, LCDR2, and LCDR3 of a bispecific antibody described herein and a second binding domain comprising an HCDR1, HCDR2, and HCDR3 and an LCDR1, LCDR2, and LCDR3 of a bispecific antibody described herein, wherein the first binding domain binds to VEGF-A and the second binding domain binds to ANG-2 and wherein the bispecific antibody reduces tumor growth, reduces tumor volume, or reduces tumor growth and reduces tumor volume as a result of being provided to a subject having a tumor. In a further embodiment the bispecific antibody is BiS3Ab-VEGF H1RK-ANG-2.

Another embodiment relates to a bispecific antibody comprising a first binding domain comprising an HCDR1, HCDR2, and HCDR3 and an LCDR1, LCDR2, and LCDR3 of a bispecific antibody described herein and a second binding domain comprising an HCDR1, HCDR2, and HCDR3 and an LCDR1, LCDR2, and LCDR3 of a bispecific antibody described herein, wherein the first binding domain binds to VEGF-A and the second binding domain binds to ANG-2 and wherein the bispecific antibody binds to ANG-2 with greater affinity than the parental ANG-2 antibody used to make the second binding domain. In a more particular embodiment, the binding affinity of the second binding domain to ANG-2 is increased by about 1-fold to about 20-fold. In a further more particular embodiment, the binding affinity of the second binding domain to ANG-2 is increased by about 1-fold, about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, or about 20-fold. In a further embodiment the bispecific antibody is BiS3Ab-VEGF H1RK-ANG-2.

Another embodiment relates to a bispecific antibody comprising a first binding domain comprising an HCDR1, HCDR2, and HCDR3 and an LCDR1, LCDR2, and LCDR3 of a bispecific antibody described herein and a second binding domain comprising an HCDR1, HCDR2, and HCDR3 and an LCDR1, LCDR2, and LCDR3 of a bispecific antibody described herein, wherein the first binding domain binds to VEGF-A and the second binding domain binds to ANG-2 and wherein the bispecific antibody has one or more or any combination of the characteristics described herein, including binding to VEGF165, binding to VEGF165 with greater affinity compared to VEGF121, binding to VEGF165 with greater affinity compared to VEGF189, binding to VEGF165 with greater affinity compared to VEGF121 and VEGF189, reducing human VEGFR2 phosphorylation, reducing murine VEGFR2 phosphorylation, reducing human and murine VEGFR2 phosphorylation, reducing human Tie2 receptor phosphorylation, reducing angiogenesis, reducing tumor growth, reducing tumor volume, reducing tumor growth and reducing tumor volume, and increasing affinity to ANG-2 through the second binding domain compared to the parental ANG-2 antibody used to make the second binding domain. In a further embodiment the bispecific antibody is BiS3Ab-VEGF H1RK-ANG-2.

Another embodiment relates to a bispecific antibody comprising an antibody heavy chain having the formula VH-CH1-H-CH2-CH3, wherein VH is a heavy chain variable domain, CH1 is a heavy chain constant region domain 1, H is a hinge region, CH2 is a heavy chain constant region domain 2, and CH3 is a heavy chain constant region domain 3. In another further embodiment, the bispecific antibody includes an antibody light chain having the formula VL-CL, wherein VL is a variable light chain domain and CL is a light chain constant domain. In another even further embodiment, the bispecific antibody has the formula VH-CH1-H-CH2-CH3 and VL-CL. In a further embodiment the bispecific antibody is BiS3Ab-VEGF H1RK-ANG-2.

Another embodiment relates to a bispecific antibody comprising the formula VH-CH1-H-CH2-CH3 and VL-CL wherein one or more scFv molecules are covalently attached to one or more N-terminal portions of the antibody heavy chain or antibody light chain. In another further embodiment the one or more scFv molecules are covalently attached to the N-terminal domain of one or more VL of the bispecific antibody. In a more particular embodiment, the bispecific antibody includes the formula VH-CH1-H-CH2-CH3 and scFv-L1-VL-CL, wherein L1 is a linker and the other various parts are previously described. In another more particular embodiment, the bispecific antibody includes the formula scFv-L1-VH-CH1-CH2-CH3 and VL-CL.

Another embodiment relates to a bispecific antibody comprising the formula VH-CH1-H-CH2-CH3 and VL-CL wherein one or more scFv molecules are covalently attached to one or more C-terminal portions of the antibody heavy chain. In a more particular embodiment, the bispecific antibody comprises the formula VH-CH1-CH2-CH3-L1-scFv and VL-CL. In another more particular embodiment, the bispecific antibody comprises the formula VH-CH1-CH2-CH3-L1-scFv-L2 and VL-CL, wherein L2 is a linker and is independent of L1 and wherein L1 and L2 are covalently bound to CH3, with the other various parts being previously described. In another further more particular embodiment, the bispecific antibody comprises the formula VH-CH1-L1-scFv-L2-CH2-CH3 and VL-CL, wherein L1 and L2 are independent linkers and wherein the heavy chain can contain a hinge region or be hingeless. In a further embodiment the bispecific antibody is BiS3Ab-VEGF H1RK-ANG-2.

In a specific embodiment, there is a bispecific antibody comprising a first binding domain comprising an HCDR1, HCDR2, and HCDR3 and an LCDR1, LCDR2, and LCDR3, wherein the first binding domain HCDR1, HCDR2, and HCDR3 and LCDR1, LCDR2, and LCDR3 comprise SEQ ID NOs: 17-22, respectively; and a second binding domain comprising an HCDR1, HCDR2, and HCDR3 and an LCDR1, LCDR2, and LCDR3, wherein the second binding domain HCDR1, HCDR2, and HCDR3 and LCDR1, LCDR2, and LCDR3 comprise SEQ ID NOs: 23-28, respectively.

In another specific embodiment, there is a bispecific antibody first binding domain comprising a heavy chain and a light chain comprising SEQ ID NOs: 3 and 9, respectively, and a second binding domain comprising a heavy chain and a light chain comprising SEQ ID NOs: 5 and 11, respectively.

In another specific embodiment, there is a bispecific antibody comprising a heavy chain amino acid sequence comprising SEQ ID NO: 1 and a light chain amino acid sequence comprising SEQ ID NO: 7.

In another specific embodiment, there is a bispecific antibody comprising a formula having the parts VH-CH1-H-CH2-CH3, VL-CL, and one or more scFv, L1, or optionally L2, wherein the formula can be:
  a. VH-CH1-CH2-CH3 and scFv-L1-VL-CL;
  b. scFv-L1-VH-CH1-CH2-CH3 and VL-CL;
  c. VH-CH1-CH2-CH3-L1-scFv and VL-CL;
  d. VH-CH1-CH2-CH3-L1-scFv-L2 and VL-CL, wherein L1 and L2 are covalently bound to CH3;
  e. VH-CH1-L1-scFv-L2-CH2-CH3 and VL-CL, the heavy chain can contain a hinge region or be hingeless.

In another specific embodiment, there is a bispecific antibody with the formula VH-CH1-CH2-CH3-L1-scFv and VL-CL.

In another specific embodiment, there is a bispecific antibody comprising a scFv comprising the amino acid sequence of SEQ ID NO: 13.

In another specific embodiment, there is a nucleic acid sequence comprising polynucleotides encoding a bispecific antibody comprising a first binding domain comprising an HCDR1, HCDR2, and HCDR3 and an LCDR1, LCDR2, and LCDR3, wherein the first binding domain HCDR1, HCDR2, and HCDR3 and LCDR1, LCDR2, and LCDR3 comprise SEQ ID NOs: 17-22, respectively; and a second binding domain comprising an HCDR1, HCDR2, and HCDR3 and an LCDR1, LCDR2, and LCDR3, wherein the second binding domain HCDR1, HCDR2, and HCDR3 and LCDR1, LCDR2, and LCDR3 comprise SEQ ID NOs: 23-28, respectively.

In another specific embodiment, there is a vector comprising polynucleotides encoding a bispecific antibody comprising a first binding domain comprising an HCDR1, HCDR2, and HCDR3 and an LCDR1, LCDR2, and LCDR3, wherein the first binding domain HCDR1, HCDR2, and HCDR3 and LCDR1, LCDR2, and LCDR3 comprise SEQ ID NOs: 17-22, respectively; and a second binding domain comprising an HCDR1, HCDR2, and HCDR3 and an LCDR1, LCDR2, and LCDR3, wherein the second binding domain HCDR1, HCDR2, and HCDR3 and LCDR1, LCDR2, and LCDR3 comprise SEQ ID NOs: 23-28, respectively.

In another specific embodiment, there is a cell comprising a vector comprising polynucleotides encoding a bispecific antibody comprising a first binding domain comprising an HCDR1, HCDR2, and HCDR3 and an LCDR1, LCDR2, and LCDR3, wherein the first binding domain HCDR1, HCDR2, and HCDR3 and LCDR1, LCDR2, and LCDR3 comprise SEQ ID NOs: 17-22, respectively; and a second binding domain comprising an HCDR1, HCDR2, and HCDR3 and an LCDR1, LCDR2, and LCDR3, wherein the second binding domain HCDR1, HCDR2, and HCDR3 and LCDR1, LCDR2, and LCDR3 comprise SEQ ID NOs: 23-28, respectively.

In another specific embodiment, there is a method of making a bispecific antibody comprising culturing a cell comprising a vector comprising polynucleotides encoding a bispecific antibody comprising a first binding domain comprising an HCDR1, HCDR2, and HCDR3 and an LCDR1, LCDR2, and LCDR3, wherein the first binding domain HCDR1, HCDR2, and HCDR3 and LCDR1, LCDR2, and LCDR3 comprise SEQ ID NOs: 17-22, respectively; and a second binding domain comprising an HCDR1, HCDR2, and HCDR3 and an LCDR1, LCDR2, and LCDR3, wherein the second binding domain HCDR1, HCDR2, and HCDR3 and LCDR1, LCDR2, and LCDR3 comprise SEQ ID NOs: 23-28, respectively.

In another specific embodiment, there is a method of reducing angiogenesis comprising providing a bispecific antibody to a subject wherein the bispecific antibody comprises a first binding domain comprising an HCDR1, HCDR2, and HCDR3 and an LCDR1, LCDR2, and LCDR3, wherein the first binding domain HCDR1, HCDR2, and HCDR3 and LCDR1, LCDR2, and LCDR3 comprise SEQ ID NOs: 17-22, respectively; and a second binding domain comprising an HCDR1, HCDR2, and HCDR3 and an LCDR1, LCDR2, and LCDR3, wherein the second binding domain HCDR1, HCDR2, and HCDR3 and LCDR1, LCDR2, and LCDR3 comprise SEQ ID NOs: 23-28, respectively.

Sequences

| SEQ ID NO | SEQUENCE | Description |
|---|---|---|
| 1 | EVQLLESGGGLVQPGGSLRLSCAASGFTFSWYEMYWVRQA PGKGLEWVSSISPSGGWTMYADSVKGRFTISRDNSKNTLYL QMNSLRAEDTAVYYCATPLYSSDGLSAGDIWGQGTMVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSREEMTKNQV SLTCLVKGFYPSDIAVEWESNGQPENNYKTTPPVLDSDGSFF LYSKLTVDKSRWQQGNVFSCSVMHEALHNHYTQKSLSLSP GKGGGGSGGGGSEIVLTQSPGTLSLSPGERATLSCRASQSIT GSYLAWYQQKPGQAPRLLITGASSWATGIPDRFSGSGSGTD FTLTISRLEPEDFAVYYCQQYSSSPITFGCGTRLEIKGGGGSG GGGSGGGGSGGGGSQVQLVESGGGVVQPGRSLRLSCAASG FTFTNYGMHWVRQAPGKCLEWVAVISHDGNNKYYVDSVK GRFTISRDNSKNTLYLQMNSLRAEDTAVYYCAREGIDFWSG LNWFDPWGQGTLVTVSS | Amino acid sequence of the heavy chain of BiS3Ab-VEGF H1RK-ANG-2 |
| 2 | GAAGTTCAATTGTTAGAGTCTGGTGGCGGTCTTGTTCAGC CTGGTGGTTCTTTACGTCTTTCTTGCGCTGCTTCCGGATTC ACTTTCTCTTGGTACGAGATGTATTGGGTTCGCCAAGCTC CTGGTAAAGGTTTGGAGTGGGTTTCTTCTATCTCTCCTTCT GGTGGCTGGACTATGTATGCTGACTCCGTTAAAGGTCGCT TCACTATCTCTAGAGACAACTCTAAGAATACTCTCTACTT GCAGATGAACAGCTTAAGGGCTGAGGACACGGCCGTGTA TTACTGTGCGACCCCCTTGTATAGCAGTGACGGGCTTTCG GCGGGGGATATCTGGGGCCAAGGGACAATGGTCACCGTC TCAAGCGCGTCGACCAAGGGCCCATCCGTCTTCCCCCTGG CACCCTCCTCCAAGAGCACCTCTGGGGGCACAGCGGCCC TGGGCTGCCTGGTCAAGGACTACTTCCCCGAACCGGTGA CGGTGTCCTGGAACTCAGGCGCTCTGACCAGCGGCGTGC ACACCTTCCCGGCTGTCCTACAGTCCTCAGGACTCTACTC CCTCAGCAGCGTGGTGACCGTGCCCTCCAGCAGCTTGGG CACCCAGACCTACATCTGCAACGTGAATCACAAGCCCAG CAACACCAAGGTGGACAAGAGAGTTGAGCCCAAATCTTG TGACAAAACTCACACATGCCCACCGTGCCCAGCACCTGA ACTCCTGGGGGGACCGTCAGTCTTCCTCTTCCCCCCAAAA CCCAAGGACACCCTCATGATCTCCCGGACCCCTGAGGTC ACATGCGTGGTGGTGGACGTGAGCCACGAAGACCCTGAG GTCAAGTTCAACTGGTACGTGGACGGCGTGGAGGTGCAT AATGCCAAGACAAAGCCGCGGGAGGAGCAGTACAACAG CACGTACCGTGTGGTCAGCGTCCTCACCGTCCTGCACCAG GACTGGCTGAATGGCAAGGAGTACAAGTGCAAGGTCTCC AACAAAGCCCTCCCAGCCCCCATCGAGAAAACCATCTCC AAAGCCAAAGGGCAGCCCCGAGAACCACAGGTCTACACC CTGCCCCCATCCCGGGAGGAGATGACCAAGAACCAGGTC AGCCTGACCTGCCTGGTCAAAGGCTTCTATCCCAGCGACA TCGCCGTGGAGTGGGAGAGCAATGGGCAGCCGGAGAAC AACTACAAGACCACGCCTCCCGTGCTGGACTCCGACGGC TCCTTCTTCCTCTATAGCAAGCTCACCGTGGACAAGAGCA GGTGGCAGCAGGGGAACGTCTTCTCATGCTCCGTGATGC ATGAGGCTCTGCACAACCACTACACGCAGAAGAGCCTCT CCCTGTCTCCGGGTAAAGGCGGAGGGGGATCCGGCGGAG GGGGCTCTGAGATCGTGCTGACCCAGAGCCCCGGCACCC TGAGCCTGAGCCCTGGCGAGAGAGCCACCCTGAGCTGCC GGGCCAGCCAGTCCATCACCGGCAGCTACCTGGCTTGGT ATCAGCAGAAGCCCGGACAGGCCCCCAGACTGCTGATCA CCGGCGCTTCCAGCTGGGCCACCGGCATCCCCGACAGAT TCAGCGGCAGCGGCTCCGGCACCGACTTCACCCTGACCA TCAGCAGACTGGAGCCCGAGGACTTCGCCGTGTACTACT GCCAGCAGTACAGCAGCAGCCCCATCACCTTCGGAtgcGG CACCAGGCTGGAGATCAAGGGCGGAGGGGGCTCTGGGG GAGGGGGCAGCGGCGGCGGAGGATCTGGGGAGGGGGC AGCCAGGTGCAGCTGGTCGAGTCTGGCGGCGGAGTGGTG CAGCCCGGCAGAAGCCTGAGACTGAGCTGCGCCGCCAGC GGCTTCACCTTCACCAACTACGGCATGCACTGGGTCCGCC AGGCCCCTGGCAAGtGCCTGGAGTGGGTGGCCGTGATCAG | Nucleotide sequence of the heavy chain of BiS3Ab-VEGF H1RK-ANG-2 |

| SEQ ID NO | SEQUENCE | Description |
|---|---|---|
| | CCACGACGGCAACAACAAGTACTACGTGGACAGCGTGAA GGGCAGATTCACCATCAGCAGGGACAACAGCAAGAACAC CCTGTACCTCCAGATGAACAGCCTGAGAGCCGAGGACAC CGCCGTGTACTACTGCGCCAGAGAGGGCATCGACTTTTG GAGCGGCCTGAATTGGTTCGACCCCTGGGGCCAGGGCAC CCTGGTGACCGTGTCCAGC | |
| 3 | EVQLLESGGGLVQPGGSLRLSCAASGFTFSWYEMYWVRQA PGKGLEWVSSISPSGGWTMYADSVKGRFTISRDNSKNTLYL QMNSLRAEDTAVYYCATPLYSSDGLSAGDIWGQGTMVTVS S | Amino acid sequence of the first binding domain heavy chain variable domain of BiS3Ab-VEGF H1RK-ANG-2 |
| 4 | GAAGTTCAATTGTTAGAGTCTGGTGGCGGTCTTGTTCAGC CTGGTGGTTCTTTACGTCTTTCTTGCGCTGCTTCCGGATTC ACTTTCTCTTGGTACGAGATGTATTGGGTTCGCCAAGCTC CTGGTAAAGGTTTGGAGTGGGTTTCTTCTATCTCTCCTTCT GGTGGCTGGACTATGTATGCTGACTCCGTTAAAGGTCGCT TCACTATCTCTAGAGACAACTCTAAGAATACTCTACTT GCAGATGAACAGCTTAAGGGCTGAGGACACGGCCGTGTA TTACTGTGCGACCCCCTTGTATAGCAGTGACGGGCTTTCG GCGGGGGATATCTGGGGCCAAGGGACAATGGTCACCGTC TCAAGC | Nucleotide sequence of the first binding domain heavy chain variable domain of BiS3Ab-VEGF H1RK-ANG-2 |
| 5 | QVQLVESGGGVVQPGRSLRLSCAASGFTFTNYGMHWVRQA PGKCLEWVAVISHDGNNKYYVDSVKGRFTISRDNSKNTLYL QMNSLRAEDTAVYYCAREGIDFWSGLNWFDPWGQGTLVT VSS | Amino acid sequence of the second binding domain heavy chain of BiS3Ab-VEGF H1RK-ANG-2 |
| 6 | CAGGTGCAGCTGGTCGAGTCTGGCGGCGGAGTGGTGCAG CCCGGCAGAAGCCTGAGACTGAGCTGCGCCGCCAGCGGC TTCACCTTCACCAACTACGGCATGCACTGGGTCCGCCAGG CCCCTGGCAAGTGCCTGGAGTGGGTGGCCGTGATCAGCC ACGACGGCAACAACAAGTACTACGTGGACAGCGTGAAGG GCAGATTCACCATCAGCAGGGACAACAGCAAGAACACCC TGTACCTCCAGATGAACAGCCTGAGAGCCGAGGACACCG CCGTGTACTACTGCGCCAGAGAGGGCATCGACTTTTGGA GCGGCCTGAATTGGTTCGACCCCTGGGGCCAGGGCACCC TGGTGACCGTGTCCAGC | Nucleotide sequence of the second binding domain of the heavy chain of BiS3Ab-VEGF H1RK-ANG-2 |
| 7 | EIVLTQSPATLSLSPGERATLSCRASQSVHSSYLAWYQQKPG QAPRLLIYGASSRATGIPDRFSGSGSGTDFTLTISRLEPEDFA VYYCQQSYRTPSFGQGTRLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | Amino acid sequence of the light chain of BiS3Ab-VEGF H1RK-ANG-2 |
| 8 | GAGATCGTGCTGACCCAGTCTCCAGCCACCCTCTCTTTGT CTCCAGGGGAAAGAGCCACCCTCTCCTGCAGGGCCAGTC AGAGTGTTCACAGCAGCTACTTAGCCTGGTACCAGCAGA AACCTGGCCAGGCTCCCAGGCTCCTCATCTATGGTGCATC CAGCAGGGCCACTGGCATCCCAGACAGGTTCAGTGGCAG TGGGTCTGGGACAGACTTCACTCTCACCATCAGCAGACTG GAGCCTGAAGATTTTGCAGTTTACTACTGTCAACAGAGTT ACCGCACCCCTTCCTTCGGCCAAGGGACACGACTGGAGA TTAAACGTACGGTGGCTGCACCATCTGTCTTCATCTTCCC GCCATCTGATGAGCAGTTGAAATCTGGAACTGCCTCTGTT GTGTGCCTGCTGAATAACTTCTATCCCAGAGAGGCCAAA GTACAGTGGAAGGTGGATAACGCCCTCCAATCGGGTAAC TCCCAGGAGAGTGTCACAGAGCAGGACAGCAAGGACAG CACCTACAGCCTCAGCAGCACCCTGACGCTGAGCAAAGC AGACTACGAGAAACACAAAGTCTACGCCTGCGAAGTCAC CCATCAGGGCCTGAGCTCGCCCGTCACAAAGAGCTTCAA CAGGGGAGAGTGT | Nucleotide sequence of the light chain of BiS3Ab-VEGF H1RK-ANG-2 |
| 9 | EIVLTQSPATLSLSPGERATLSCRASQSVHSSYLAWYQQKPG QAPRLLIYGASSRATGIPDRFSGSGSGTDFTLTISRLEPEDFA VYYCQQSYRTPSFGQGTRLEIK | Amino acid sequence of the first binding domain light chain variable domain of BiS3Ab-VEGF H1RK-ANG-2 |

-continued

| SEQ ID NO | SEQUENCE | Description |
|---|---|---|
| 10 | GAGATCGTGCTGACCCAGTCTCCAGCCACCCTCTCTTTGT CTCCAGGGGAAAGAGCCACCCTCTCCTGCAGGGCCAGTC AGAGTGTTCACAGCAGCTACTTAGCCTGGTACCAGCAGA AACCTGGCCAGGCTCCCAGGCTCCTCATCTATGGTGCATC CAGCAGGGCCACTGGCATCCCAGACAGGTTCAGTGGCAG TGGGTCTGGGACAGACTTCACTCTCACCATCAGCAGACTG GAGCCTGAAGATTTTGCAGTTTACTACTGTCAACAGAGTT ACCGCACCCCTTCCTTCGGCCAAGGGACACGACTGGAGA TTAAA | Nucleotide sequence of the first binding domain light chain variable domain of BiS3Ab-VEGF H1RK-ANG-2 |
| 11 | EIVLTQSPGTLSLSPGERATLSCRASQSITGSYLAWYQQKPG QAPRLLITGASSWATGIPDRFSGSGSGTDFTLTISRLEPEDFA VYYCQQYSSSPITFGCGTRLEIK | Amino acid sequence of the second binding domain light chain domain of BiS3Ab-VEGF H1RK-ANG-2 |
| 12 | GAGATCGTGCTGACCCAGAGCCCCGGCACCCTGAGCCTG AGCCCTGGCGAGAGAGCCACCCTGAGCTGCCGGGCCAGC CAGTCCATCACCGGCAGCTACCTGGCTTGGTATCAGCAG AAGCCCGGACAGGCCCCCAGACTGCTGATCACCGGCGCT TCCAGCTGGGCCACCGGCATCCCCGACAGATTCAGCGGC AGCGGCTCCGGCACCGACTTCACCCTGACCATCAGCAGA CTGGAGCCCGAGGACTTCGCCGTGTACTACTGCCAGCAG TACAGCAGCAGCCCCATCACCTTCGGAtgcGGCACCAGGC TGGAGATCAAG | Nucleotide sequence of the second binding domain light chain domain of BiS3Ab-VEGF H1RK-ANG-2 |
| 13 | EIVLTQSPGTLSLSPGERATLSCRASQSITGSYLAWYQQKPG QAPRLLITGASSWATGIPDRFSGSGSGTDFTLTISRLEPEDFA VYYCQQYSSSPITFGCGTRLEIKGGGGSGGGGSGGGGSGG GSQVQLVESGGGVVQPGRSLRLSCAASGFTFTNYGMHWVR QAPGKCLEWVAVISHDGNNKYYVDSVKGRFTISRDNSKNT LYLQMNSLRAEDTAVYYCAREGIDFWSGLNWFDPWGQGT LVTVSS | Amino acid sequence of the scFv of BiS3Ab-VEGF H1RK-ANG-2 |
| 14 | GAGATCGTGCTGACCCAGAGCCCCGGCACCCTGAGCCTG AGCCCTGGCGAGAGAGCCACCCTGAGCTGCCGGGCCAGC CAGTCCATCACCGGCAGCTACCTGGCTTGGTATCAGCAG AAGCCCGGACAGGCCCCCAGACTGCTGATCACCGGCGCT TCCAGCTGGGCCACCGGCATCCCCGACAGATTCAGCGGC AGCGGCTCCGGCACCGACTTCACCCTGACCATCAGCAGA CTGGAGCCCGAGGACTTCGCCGTGTACTACTGCCAGCAG TACAGCAGCAGCCCCATCACCTTCGGAtgcGGCACCAGGC TGGAGATCAAGGGCGGAGGGGGCTCTGGGGGAGGGGGC AGCGGCGGCGGAGGATCTGGGGGAGGGGGCAGCCAGGT GCAGCTGGTCGAGTCTGGCGGCGGAGTGGTGCAGCCCGG CAGAAGCCTGAGACTGAGCTGCGCCGCCAGCGGCTTCAC CTTCACCAACTACGGCATGCACTGGGTCCGCCAGGCCCCT GGCAAGtGCCTGGAGTGGGTGGCCGTGATCAGCCACGAC GGCAACAACAAGTACTACGTGGACAGCGTGAAGGGCAG ATTCACCATCAGCAGGGACAACAGCAAGAACACCCTGTA CCTCCAGATGAACAGCCTGAGAGCCGAGGACACCGCCGT GTACTACTGCGCCAGAGAGGGCATCGACTTTTGGAGCGG CCTGAATTGGTTCGACCCCTGGGGCCAGGGCACCCTGGT GACCGTGTCCAGC | Nucleotide sequence of the scFv of BiS3Ab-VEGF H1RK-ANG-2 |
| 15 | GGGGSGGGGSGGGGSGGGGS | Amino acid sequence of the linker within the scFV |
| 16 | GGGGSGGGGS | Amino acid sequence of the linker between the CH3 domain and the scFv |
| 17 | WYEMY | HCDR1 amino acid sequence of the first binding domain of BiS3Ab-VEGF H1RK-ANG-2 |
| 18 | SISPSGGWTMYADSVKG | HCDR2 amino acid sequence of the first binding domain of BiS3Ab-VEGF H1RK-ANG-2 |
| 19 | PLYSSDGLSAGDI | HCDR3 amino acid sequence of the first binding domain of BiS3Ab-VEGF H1RK-ANG-2 |

-continued

Sequences

| SEQ ID NO | SEQUENCE | Description |
|---|---|---|
| 20 | RASQSVHSSYLA | LCDR1 amino acid sequence of the first binding domain of BiS3Ab-VEGF H1RK-ANG-2 |
| 21 | GASSRAT | LCDR2 amino acid sequence of the first binding domain of BiS3Ab-VEGF H1RK-ANG-2 |
| 22 | QQSYRTPS | LCDR3 amino acid sequence of the first binding domain of BiS3Ab-VEGF H1RK-ANG-2 |
| 23 | GFTFTNYGMH | HCDR1 amino acid sequence of the second binding domain of BiS3Ab-VEGF H1RK-ANG-2 |
| 24 | VISHDGNNKYYVDSVKG | HCDR2 amino acid sequence of the second binding domain of BiS3Ab-VEGF H1RK-ANG-2 |
| 25 | EGIDFWSGLNWFDP | HCDR3 amino acid sequence of the second binding domain of BiS3Ab-VEGF H1RK-ANG-2 |
| 26 | RASQSITGSYLA | LCDR1 amino acid sequence of the second binding domain of BiS3Ab-VEGF H1RK-ANG-2 |
| 27 | GASSWAT | LCDR2 amino acid sequence of the second binding domain of BiS3Ab-VEGF H1RK-ANG-2 |
| 28 | QQYSSSPIT | LCDR3 amino acid sequence of the second binding domain of BiS3Ab-VEGF H1RK-ANG-2 |

EXAMPLES

For the experiments described herein various antibodies were used, including MEDI3617 (Int J Oncol. 2012 May; 40(5):1321-30), Avastin® (Ferrara, N et al. Biochem Biophys Res Comm, 333:328-335, 2005), G6-31 (Liang, W C et al. J Biol Chem, 281: 951-961, 2006), B20-4.1 (Liang, W C et al. J Biol Chem, 281: 951-961, 2006), and an isotype control, designated R347, as a monospecific or a bispecific antibody as needed. An anti-VEGF IgG1 antibody capable of binding all VEGF isoforms that is not cross-reactive with mouse can used as a positive control for some binding and functional studies. Where cross reactivity to mouse VEGF is needed the antibodies G6-31 and B20-4.1 can be used as a positive control.

Example 1—Format and Sequence of Bs3Ab-Vegf H1Rk-Ang2

BiS3Ab-VEGF H1RK-ANG-2 was designed to concurrently reduce one or more biological activities of VEGF-A and ANG-2 by reducing binding to their receptors, VEGFR and Tie2 respectively. FIG. 2 is a schematic diagram of BiS3Ab-VEGF H1RK-ANG-2. The bispecific bivalent antibody is comprised of a full-length IgG molecule with a scFv linked to the C-terminus of each heavy chain as previously described by Dimasi et. al. (J Mol Biol. 2009). The binding specificity of the Fab region is anti-VEGF-A (first binding domain) and the scFv is anti-ANG-2 (second binding domain). The entire nucleotide sequence encoding the light chain of the first binding domain is shown in FIG. 3. The translated amino acid sequence and the light chain variable region amino acid sequence is also shown in FIG. 3. The anti-VEGF light chain was germline corrected at position 107 by mutating a threonine to lysine. The germline corrected anti-VEGF sequence is referred to as H1RK. The complete nucleotide sequence of the heavy chain is shown in FIG. 4 and the corresponding amino acid sequence is shown in FIG. 5. The amino acid sequence of the heavy chain sequence can be further divided into the heavy chain variable region of the first binding domain, the heavy chain constant region including the CHL CH2 and CH3 domain, the connecting glycine serine linker, the variable light chain of the second binding domain, the scFv glycine serine linker and the variable heavy region of the second binding domain.

Example 2—Transient Transfection

Transient transfection of BiS3Ab-VEGF H1RK-ANG-2 and the parental antibodies were carried out in HEK 293F suspension cells cultured in FreeStyle™ serum-free media (Invitrogen) at 120 rpm, 37° C. and 8% CO2. The cells were split to $0.7 \times 10^6$ one day prior transfection. 300 of 293Fectin™ transfection reagent (Invitrogen) and 200 µg of the DNA was separately diluted into 5 mL of Opti-MEM® I Reduced Serum Medium (Invitrogen) and incubated for five minutes at room temperature. The DNA and 293Fectin™ mixture was combined and incubated for an additional 30 minutes and then added to 300 mL of 1×10⁶ HEK 293F cells per mL. The volume of the transfected culture was doubled every third day with FreeStyle™ serum-free media. The culture was harvested on the eleventh day by centrifugation for 10 minutes 1500×g and 0.2 mM filtered (Eppendorf).

Expression of BiSAb-VEGF H1RK-ANG-2 and parental antibodies were monitored using a protein A binding method. An aliquot of the cultured media was 0.2 µm filter (Eppendorf) and loaded onto a protein A column (POROS® A 20 µm Column, 4.6×50 mm, 0.8 mL) using a HPLC system (Agilent 1100 Capillary LC). The column was washed with 1×PBS pH 7.2, and antibodies were eluted with 0.1% phosphoric acid (pH 1.8). The area under the eluted peak, determine by integrating the UV signal at A280 nm, was measured and used to calculate the expression level by compared to a known IgG standard. Table 1 shows the expression level of the parental antibodies and BiSAb-VEGF H1RK-ANG-2.

TABLE 1

|  | Anti-VEGF mAb | Anti-ANG-2 mAb | BiSAb-VEGF H1RK-ANG-2 |
| --- | --- | --- | --- |
| Transient expression (after day 10 in 293 F. (mg/L) | 195 | 165 | 174 |

Example 3—Protein Purification and Concentration Determination

Antibodies were purified by standard protein A affinity chromatography methods. One liter of conditioned media was centrifuged at 1500×g for 10 minutes and 0.2 µM vacuum filtered (Nalgene). The filtered supernatant was loaded onto a mAbselect™ protein A columns (GE) using an Akta Explorer (GE). The protein A column was equilibrated with 20 column volumes of 1×PBS, pH 7.2 and the filtered culture media was loaded using a flow rate of 5 mL/min. Unbound material was removed by using 20 column volumes of 1×PBS, pH 7.2. Antibody elution was carried out using 10 column volumes of 0.1M glycine, 150 mM sodium chloride pH 3.2. The elution was monitored using absorbance of 280 nm. The protein A eluted antibodies were immediately neutralized by using 1/10 of volume per fraction of 1 M Tris-HCl pH 7.0. The antibodies were then filtered using a 0.22 µM syringe filter (Nalgene). The concentration of the purified antibodies was determined by reading the absorbance at 280 nm using a NanoDrop (NanoDrop) and an extinction coefficient of 1.4 $M^{-1}$ $cm^{-1}$.

Aggregate generated during the expression of the BiSAb-VEGF H1RK-ANG-2 can be efficiently removed by Ceramic Hydroxyapatite type II (GE) purification. The CHT column was pre-conditioned with five column volumes of 1M sodium hydroxide and neutralize to pH 7.2 with 1×PBS pH 7.2 at 5 mL/min. 20 column volumes of buffer A (20% 1×PBS, pH 7.2 in sterile water) was used to equilibrate the column prior to use. BiSAb-VEGF H1RK-ANG-2 protein A eluant was directly loaded on the CHT column and washed with 20 column volumes of buffer A. The monomer fraction was eluted with 15% buffer A and 85% buffer B (5×PBS, pH 7.2) for 15 column volumes. The aggregate was eluted using 100% buffer B. A representative elution profile is shown in FIG. 6. The monomer fraction was dialyzed overnight in 1×PBS, pH 7.2.

Figure 7:
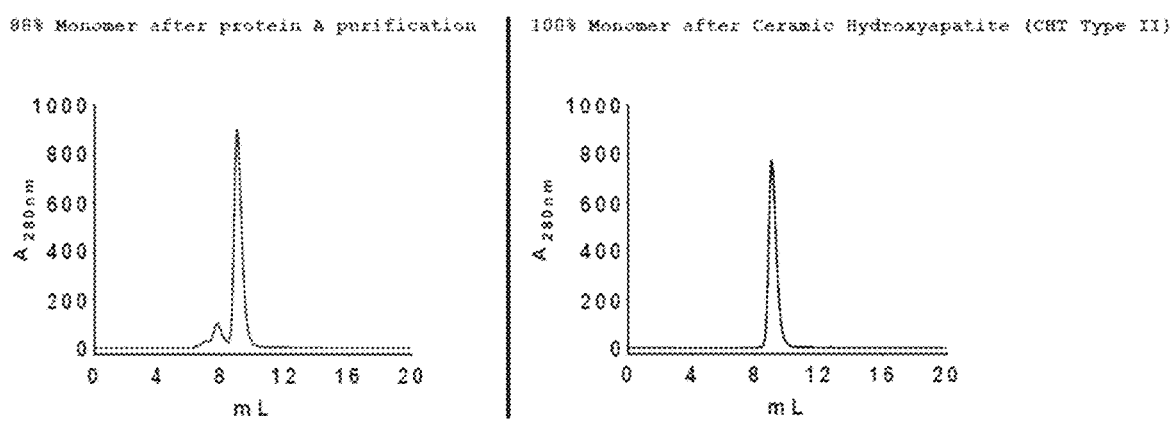
FIG. 7 depicts representative data for purification profiles for the bispecific antibody BiSAb-VEGF H1RK-ANG-2.

Monomeric content of the BiS3Ab-VEGF H1RK-ANG-2 was measured after the protein A purification to determine the aggregate level and if a polishing step is needed. Analytical size-exclusion chromatography (SEC-HPLC) was carried out using an Agilent 1100 HPLC (Agilent) with a TSK GEL G3000SWXL column (Tosoh Bioscience). 250 µg of bispecific antibodies were used for the analysis. The mobile phase used was 0.1 M sodium sulfate, 0.1 M sodium phosphate pH 6.8, and antibodies were monitored using an absorbable of 280 nm. Chemstation software (Agilent) was used for the analysis and the figures were prepared using Prism5 software (GraphPad). A representative monomeric content after protein purification and after ceramic hydroxyapatite purification is shown in FIG. 7. At least 12% of aggregates in BiS3Ab-VEGF H1RK-ANG-2 can efficiently be removed by using ceramic hydroxyapatite chromatography.

Example 4—Analytical Characterization of Bisab-Vegf H1Rk-Ang-2

Figure 8:
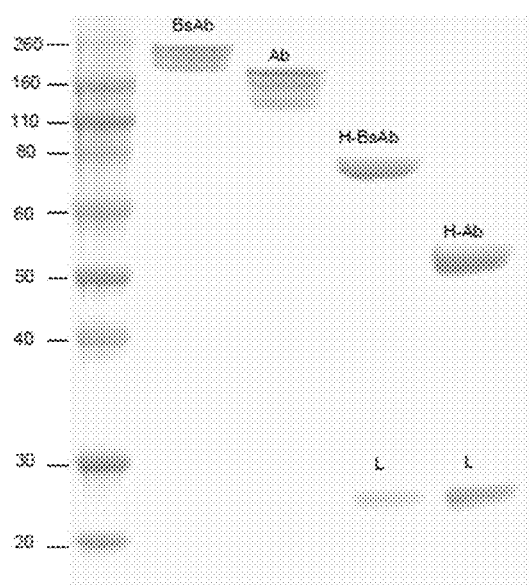
FIG. 8 depicts representative SDS-PAGE gel for the bispecific antibody BiS3Ab-VEGF H1RK-ANG-2. BsAb—Intact BiS3Ab-VEGF H1RK-ANG-2; Ab—Anti-VEGF mAb; H-BsAb-Heavy chain of BiS3Ab-VEGF H1RK-ANG-2; H-Ab—Heavy chain of anti-VEGF mAb; L—Light chian of BiS3Ab-VEGF H1RK-ANG-2 and anti-VEGF.

BiS3Ab-VEGF H1RK-ANG-2 was analyzed by reducing and non-reducing SDS-PAGE. 2 µg of protein, anti-VEGF or BiS3Ab-VEGF H1RK-ANG-2, in 15 µL of 1×PBS pH 7.2 and mixed with 5 µL of LDS-PAGE loading buffer, with and without 1×NuPAGE reducing agent (Invitrogen). 10 µL of the Novex Sharp Pre-Stained Protein Standard (Invitrogen) was used as a protein ladder. The samples were heated at 70° C. for 10 minutes, spun down at 13,500 rpm using a benchtop centrifuge and loaded onto 4-12% Nupage gel (Invitrogen). Electrophoresis was carried out in MOPS buffer at 200 volts for one hour. The SDS-PAGE gels were stained with SimplyBlue™ SafeStain (Invitrogen) and de-stained in water overnight. A representative SDS-PAGE gel is shown in FIG. 8.

Figure 9:
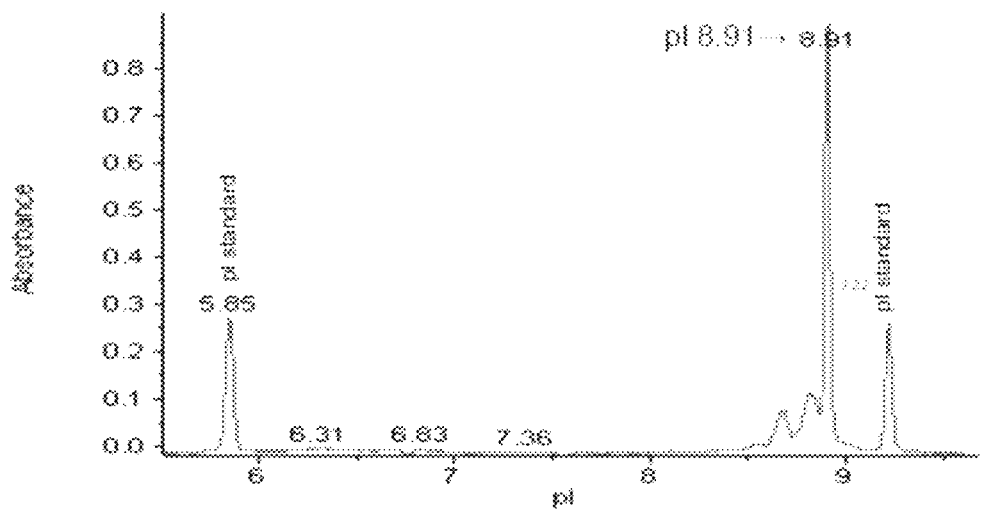
FIG. 9 depicts representative data after focusing for the bispecific antibody BiS3Ab-VEGF H1RK-ANG-2.

Imaged capillary isoelectric focusing of BiS3Ab-VEGF H1RK-ANG-2 was performed using an iCE2 analyzer (ProteinSimple). The pharmalytes pH 3-10 and 8-10.5 was obtained from Sigma. The FC cartridge Chemical Testing Kit for the performance evaluation of the iCE3 Analyzer, including anolyte (80 mM phosphoric acid in 0.1% methyl cellulose), catholyte (100 mM sodium hydroxide in 0.1%% methyl cellulose), 0.5% methylcellulose, hemoglobin and ampholytes and pI markers in 0.35% methyl cellulose were purchased from ProteinSimple. 5.85 and 9.46 pI markers were obtained from ProteinSimple. The FC cartridge separation used was purchased from ProteinSimple BiS3Ab-VEGF H1RK-ANG-2 was prepared at 1 mg/mL in deionized water. 50 µl of 1 mg/ml Bs3Ab-VEGF-Ang2 solution, 2 µl of 5.85 pI marker, 2 µl of 9.46 pI marker, 140 µl of 0.5% methylcellulose, 2 µl of pharmalytes 3-10 and 6 µl of 8-10.5 pharmalytes were combined; vortex for 45 sec and centrifuged at 10,000 rpm for 3 minutes. Sample was introduced to the capillary using an autosampler (ProteinSimple). Sample separation was performed by pre-focus at 1000 kV for 1 minute/s followed by 3000 kV for 7 minute/s. Detection was carried out with a deuterium lamp detector at 280 nm. Data were analyzed and figures were prepared using the iCE280 analyzer software. Representative focusing of BiS3Ab-VEGF H1RK-ANG-2 is shown in FIG. 9; the pI of the protein is indicated.

Figure 10:
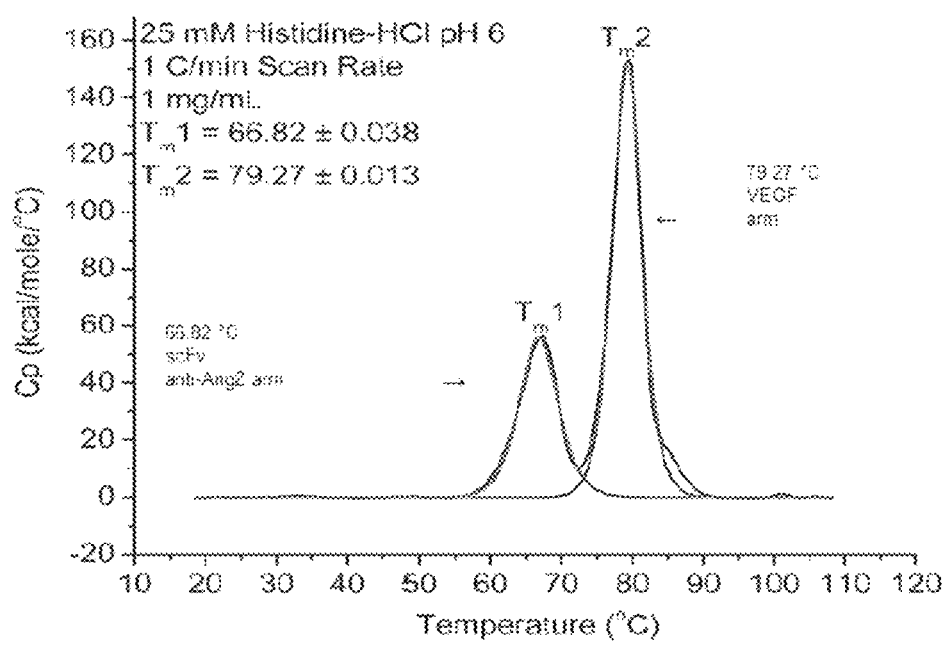
FIG. 10 depicts representative data for transition temperatures for the bispecific antibody BiS3Ab-VEGF H1RK-ANG-2.

BiS3Ab-VEGF H1RK-ANG-2 was dialyzed three times overnight in 25 mM Histidine pH 6.0 prior to differential scanning calorimetry analysis using a VP-DSC (Microcal). The final dialysis buffer was used for reference scans to obtain a stable base line for reference subtraction. The reagents were degassed for a minimum of two minutes and proteins were diluted to 1 mg/mL in reference buffer and scanned at 1° C./min from 20° C. to 110° C. using a 16 seconds filter period. Representative transition temperatures for BiS3Ab-VEGF H1RK-ANG-2 are shown in FIG. 10.

Example 5—Binding Affinity of Bis3Ab-Vegf H1Rk-Ang-2 to Ang-2

BiS3Ab-VEGF H1RK-ANG-2 binding affinity to ANG-2 was determined. Equilibrium binding constants (KD) were obtained from measurements made on KinExA 3000 and 3200 instruments (Sapidyne Instruments, Boise, Id.). Human ANG-2 (huAng2) protein was coated onto Ultra-Link® Biosupport beads (PIERCE, Rockford, Ill.) at concentrations of 5 mg/mL and 30 mg/mL in coating buffer (50 mM sodium carbonate buffer, pH 9). Coated beads were then separated (gentle pulse spin) from unreacted huAng2 protein solution, and blocked with 1M Tris, pH 8, containing BSA at 10 mg/mL) for approximately 15 minutes at room temperature. After this, the bead slurry was spun to remove the blocking solution, and then the block step was repeated for approximately 2 hours using fresh block buffer, and stored at 4° C. until used. Prior to use, the huAng2-coated beads were transferred to a bead vial, resuspended in approximately 27 mLs of instrument buffer (HBS-P buffer, pH 7.4; contains 10 mM HEPES, 0.15M NaCl, 0.005% P20+0.02% NaN3), and affixed to the KinExA instrument. Briefly, solutions of BiS3Ab-VEGF H1RK-ANG-2 were prepared at 4 pM, 40 pM and 400 pM in instrument buffer (HBS-P buffer), then dispensed into three separate series of 13 tubes. These concentrations of bispecific antibody were chosen to allow measurements to be made under both receptor- and KD-controlled conditions, which would allow for more rigorous estimations of reagent activity and affinity, respectively. Two-fold serial dilutions of huAng2 protein were then titrated across nine of the tubes containing the bispecific solutions, followed by 10-fold-dilutions across two more tubes, leaving one tube as the bispecific-only, "zero" control. In so doing, this yielded concentration series' of huAng2protein that ranged from 39 fM-2 nM (4 pM bispecific experiment), 156 pM-8 nM (40 pM and 400 pM bispecific experiments). Based on theory curve simulations available through the vendor software (Sapidyne Instruments, Boise, Id.), the mixtures were incubated 1-3 days at room temperature to allow binding to reach equilibrium. At the end of this time, signal-testing experiments were conducted to determine the appropriate run conditions for each set of measurements. Detection of free antibody was made possible using a species-specific, secondary antibody reagent (Goat Anti-Human IgG (H+L)-DyLight649, Part #109-495-088, Jackson ImmunoResearch Laboratories), employed at 0.75 mg/mL or 1.0 mg/mL in instrument buffer containing BSA at 1 mg/mL. Data obtained from all sets of measurements was then simultaneously fitted to a one-site binding model using the software's' n-Curve analysis feature to obtain the equilibrium binding constant (KD) as reported in Table 2.

TABLE 2

| Ligand | | $K_D$, pM (95% CI) (Std. Aff. model - ref [Ligand]) | Fit Error | Binding Site Activity | $*K_D$, pM (Alternate model - ref [IgG]) |
|---|---|---|---|---|---|
| BiSAb-VEGF H1RK-ANG-2 | huVEGF | 24.0 (17.3-34.2) | 3.06% | 80% | 30.1 |

TABLE 2-continued

| Ligand | | $K_D$, pM (95% CI) (Std. Aff. model - ref [Ligand]) | Fit Error | Binding Site Activity | $*K_D$, pM (Alternate model - ref [IgG]) |
|---|---|---|---|---|---|
| BiSAb-VEGF H1RK-ANG-2 | huAng2 | 23.3 (11.2-41.7) | 3.67% | 536% | 4.35 |

BiSAb-VEGF H1RK-ANG-2 binding affinity to VEGF was determined. As with the anti-hu-Ang2 measurements, equilibrium binding constants (KD) measurements were performed on KinExA 3000 and 3200 instruments (Sapidyne Instruments, Boise, Id.). Human VEGF (huVEGF) protein was coated onto UltraLink® Biosupport beads (PIERCE, Rockford, Ill.) at concentrations of 3 mg/mL, 30 mg/mL and 50 mg/mL in coating buffer (50 mM sodium carbonate buffer, pH 9). Coated beads were then separated (gentle pulse spin) from unreacted huVEGF protein solution, and blocked with 1M Tris, pH8, containing BSA at 10 mg/mL) for approximately 15 minutes at room temperature. After this, the bead slurry was spun to remove the blocking solution, and then the block step was repeated for approximately 2 hours using fresh block buffer, and stored at 4° C. until used. Prior to use, the huAng2-coated beads were transferred to a bead vial, resuspended in approximately 27 mLs of instrument buffer (10 mM HEPES+300 mM NaCl+5 mM CaCl2+0.05% P20+0.02% NaN3, pH8), and affixed to the KinExA instrument. Briefly, solutions BiSAb-VEGF H1RK-ANG-2 were prepared at 10 pM, 100 pM and 2.5 nM in instrument buffer, then dispensed into three separate series of 13 tubes. These concentrations of bispecific were chosen to allow measurements to be made under both receptor- and KD-controlled conditions, which would allow for more rigorous estimations of reagent activity and affinity, respectively. Two-fold serial dilutions of huVEGF protein were then titrated across nine of the tubes containing the bispecific solutions, followed by 10-fold-dilutions across two more tubes, leaving one tube as the bispecific-only, "zero" control. In so doing, this yielded concentration series' of huVEGF protein that ranged from 78 fM-4 nM (10 pM bispecific experiment), 488 fM-25 nM (100 pM bispecific experiment), and 3.91 pM-200 nM (2.5 nM bispecific experiment). Based on theory curve simulations available through the vendor software (Sapidyne Instruments, Boise, Id.), the mixtures were incubated 1-4 days at room temperature to allow binding to reach equilibrium. At the end of this time, signal-testing experiments were conducted to determine the appropriate run conditions for each set of measurements. Detection of free antibody was made possible using a species-specific, secondary antibody reagent (Goat Anti-Human IgG (H+L)-DyLight649, Part #109-495-088, Jackson ImmunoResearch Laboratories), employed at 0.75 mg/mL, 1.0 mg/mL or 2 mg/mL in instrument buffer containing BSA at 1 mg/mL. Data obtained from all sets of measurements was then simultaneously fitted to a one-site binding model using the software's' n-Curve analysis feature to obtain the equilibrium binding constant (KD) as reported above in Table 2.

Example 6—Concurrent Binding by Bis3Ab-Vegf H1Rk-Ang-2 to Ang-2 and Vegf165

Figure 11:
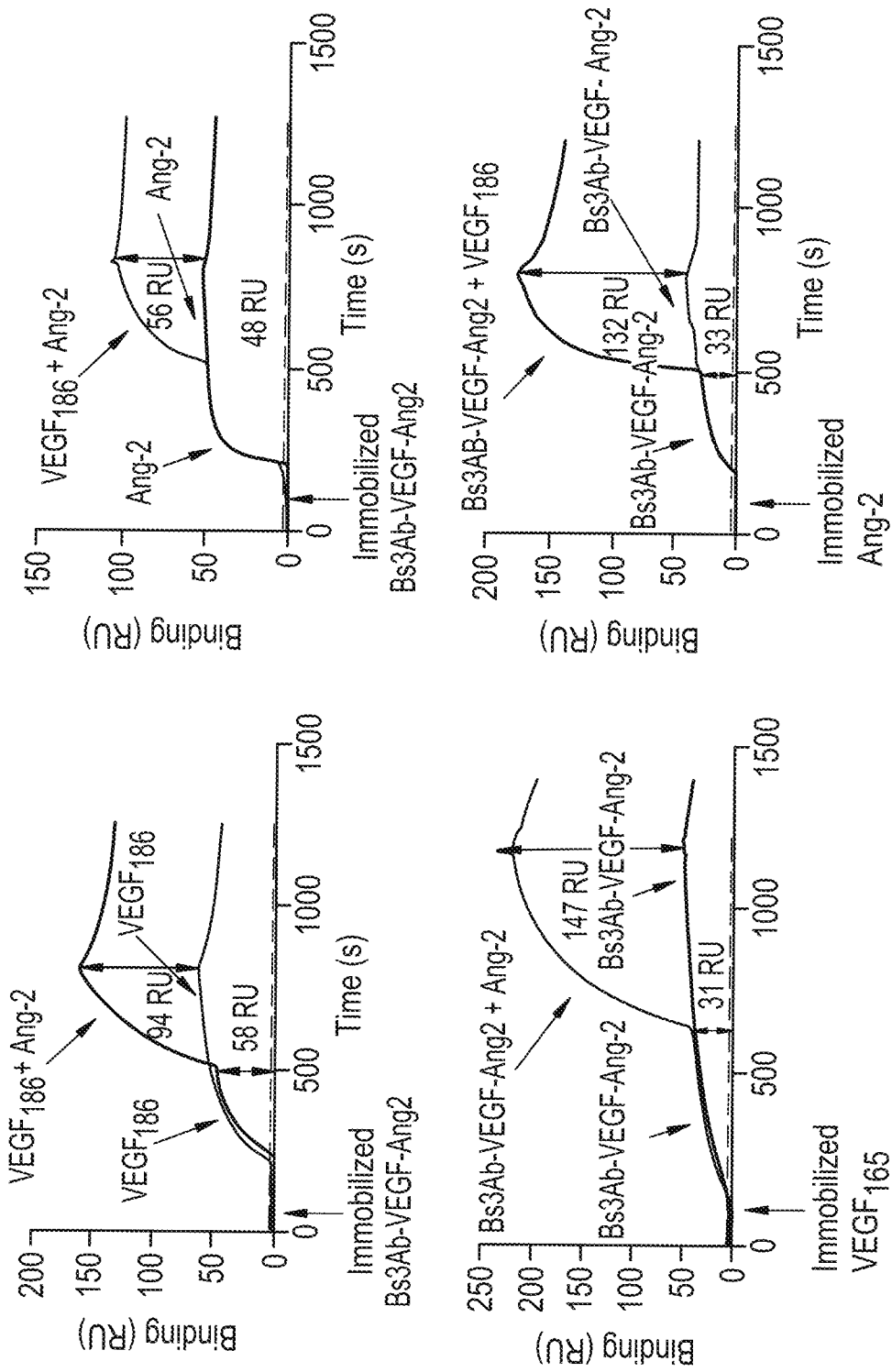
FIG. 11 depicts representative data for concurrent binding of the bispecific antibody BiSAb-VEGF H1RK-ANG-2 to VEGF-165 and ANG-2.

Concurrent binding experiments were performed on a Biacore 3000 (GE Healthcare) at 25° C. using 10 nM of VEGF165, 100 nM of Ang2 and 10 nM of Bs3Ab-VEGF-Ang2 in 10 mM Acetate, pH 5 and immobilized to on CM5 sensorchip surfaces, using standard amine coupling protocols provided by the manufacturer (GE Healthcare). Using the solutions BiSAb-VEGF H1RK-ANG-2 immobilized chip, 100 nM of VEGF and a mixture of 100 nM of VEGF and 500 nM of ANG-2 were prepared in HBS buffer (GE Healthcare). The VEGF solution was injected at a flow rate of 30 mL/min for 500 seconds. An additional injection of VEGF or the VEGF/ANG-2 mixture was injected for 250 seconds after the first injection. A similar experiment was done by first injecting 500 nM of ANG-2 followed by another ANG-2 injection of the VEGF/ANG-2 mixture. To further confirm concurrent binding, the VEGF and ANG-2 coated chips were used. For the VEGF165 surface, 50 nM of BiSAb-VEGF H1RK-ANG-2 was flowed at 30 mL/min for 600 seconds followed by a second injection of 50 nM BiSAb-VEGF H1RK-ANG-2 and 500 nM of ANG-2. The ANG-2 surface was used for a similar experiment. 50 nM of BiSAb-VEGF H1RK-ANG-2 was used for the initial injection for 500 seconds at 30 mL/min. The second injection was done using either 50 nM of BiSAb-VEGF H1RK-ANG-2 of a mixture of BiSAb-VEGF H1RK-ANG-2 and 100 nM of VEGF165. The data were analyzed using BIAevaluation (GE healthcare) and the figure was prepared using Prism 5 (Graph Pad) and representative results are shown in FIG. 11.

Figure 12A:
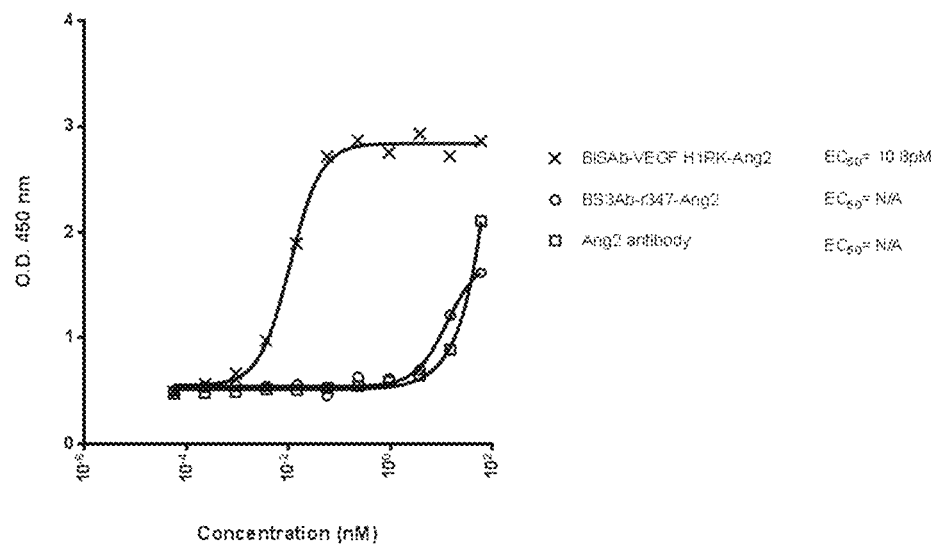
FIG. 12A depicts representative data for concurrent binding of the bispecific antibody BiSAb-VEGF H1RK-ANG-2 to VEGF-165 and ANG-2 using an ELISA based assay.
Figure 12B:
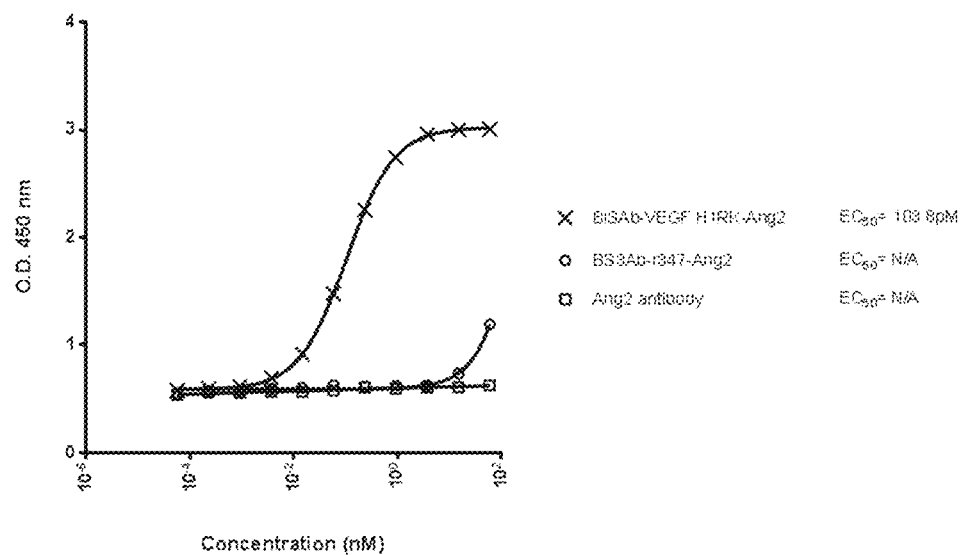
FIG. 12B depicts representative data for concurrent binding of the bispecific antibody BiSAb-VEGF H1RK-ANG-2 to VEGF-165 and ANG-2 using an ELISA based assay.
Figure 13:
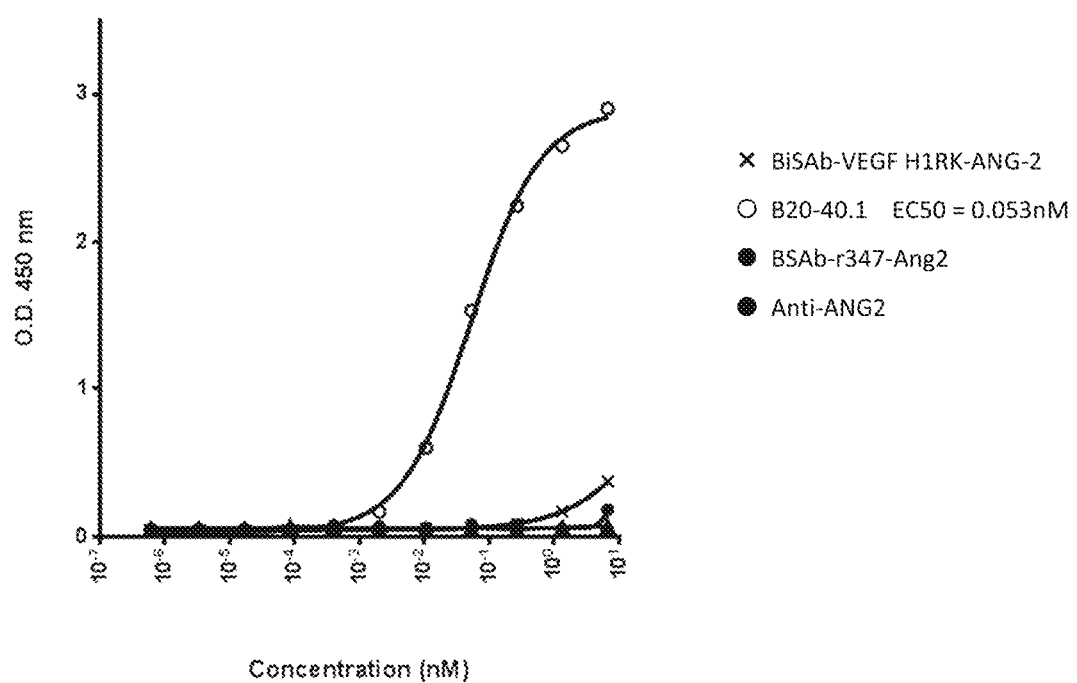
FIG. 13 depicts representative data showing lack of binding to VEGF121 by the bispecific antibody BiSAb-VEGF H1RK-ANG-2.
Figure 14:
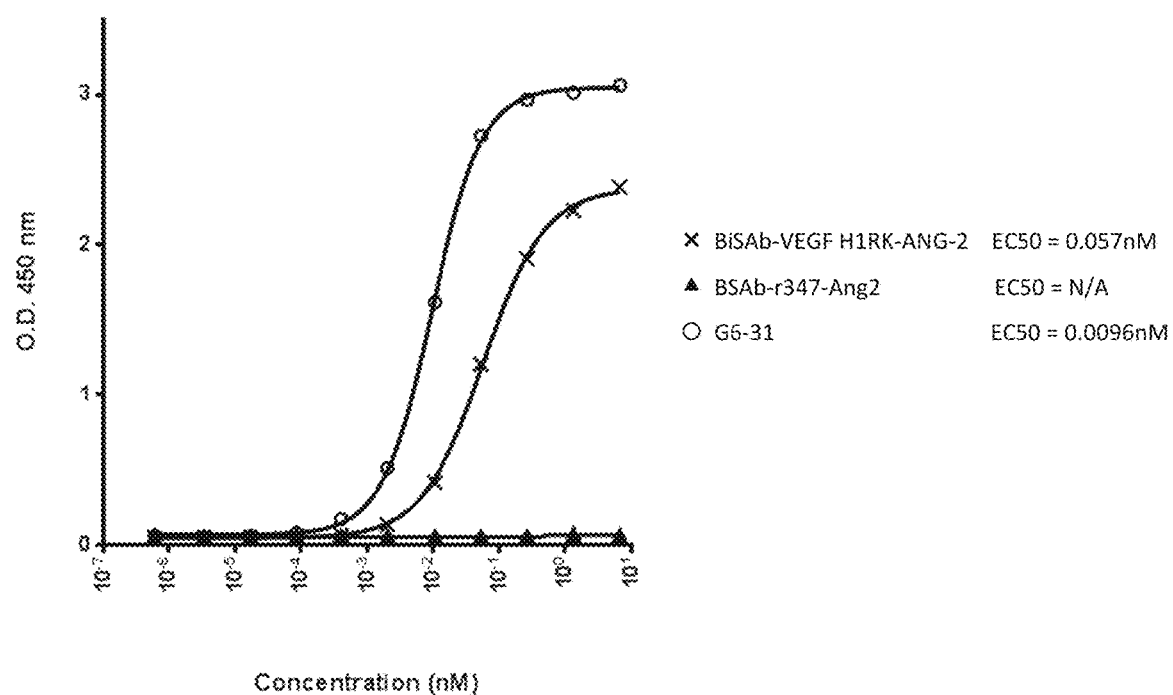
FIG. 14 depicts representative data showing lack of binding to VEGF189 by the bispecific antibody BiSAb-VEGF H1RK-ANG-2.

BiSAb-VEGF H1RK-ANG-2 antibodies were also screened for concurrent binding to VEGF and ANG-2 in a dual binding ELISA. Maxisorp plates (Nunc, Cat #439454) were coated with 100 µl of 1.0 µg/mL human or mouse VEGF (Peprotech) diluted in PBS without Ca++ or Mg++ and refrigerated overnight. Plates were decanted, then blocked for 1.5 hours with 200 µl of Blocking Buffer containing 3% BSA (Sigma, Cat #A-3059) and 0.1% Tween-20 in 1×PBS on a plate shaker. Plates were washed 3 times with 1×PBS containing 0.1% Tween-20. 50 µl of 60 nM and serial dilutions of BiSAb-VEGF H1RK-ANG-2 bispecific antibodies, Ang-2 antibody, or bispecific with r347 isotype control arm (BS3Ab-r347-Ang2) in blocking buffer were added in duplicate and incubated for 1 hour on a plate shaker. Plates were washed 3 times with wash buffer, then 50 µl of 1 µg/ml human or mouse Ang2-biotin (R&D Systems) in blocking buffer was added to each well and incubated at room temperature for 1 hour on a plate shaker. Plates were washed, then 50 µl of 1:15,000 streptavidin HRP (Pierce) was added for 1 hour at room temperature on a plate shaker. Plates were washed, then developed by adding 50 µl of TMB solution (KPL) to each well, then stopping the reaction with 50 µl of 1M phosphoric acid. Plates were read at 450 nm using a microplate reader. EC50 values were determined using non-linear regression analysis (log dose response, 4-parameter fit curves) in GraphPad Prism, version 5.01 (San Diego, Calif.). Representative results are shown in FIG. 12A (human) and FIG. 12B (mouse). Strong concurrent binding to human and mouse VEGF and ANG-2 was exhibited by BiSAb-VEGF H1RK-ANG-2 (EC50 10.8 pM and 103.8 pM, respectively), compared to the Ang2 antibody (MEDI3617) alone and BS3Ab-r347-Ang2 which showed weak binding in this assay, denoting failure to bind VEGF and ANG-2 at the same time.

Example 7—Screening of Bisab-Vegf H1Rk-Ang-2 for Reduced Vegf121 Binding

Antibodies were screened for VEGF121 binding in an ELISA format. 96-well half well maxisorp plates were coated with 25 μl of 2 μg/mL human VEGF (Peprotech) diluted in PBS without Ca++ or Mg++ and refrigerated overnight. Plates were decanted, then blocked for 1.5 hours at 37° C. with 180 μl of Blocking Buffer containing 3% BSA (Sigma, Cat #A-3059) and 0.1% Tween-20 in 1×PBS. Plates were washed 3 times with 1×PBS containing 0.1% Tween-20. 50 μl serial dilutions of anti-VEGF antibodies, Avastin® (positive control; anti-VEGF antibody) and r347 (negative control) in blocking buffer were added in duplicate and incubated at 37° C. for 1 hour. Plates were washed 3 times with wash buffer, then 50 μl of 1:5000 goat anti-human HRP IgG H+L (Jackson Immunoresearch) was added to each well and incubated at room temperature for 1 hour. Plates were developed by adding 50 μl of TMB solution (KPL) to each well, then stopping the reaction with 50 μl of 1M phosphoric acid. Plates were read at 450 nm using a microplate reader. Representative results are shown in FIG. 13. BiSAb-VEGF H1RK-ANG-2 lacked VEGF121 binding, in contrast to the positive control B20-4.1.

Example 8—Screening of Bisab-Vegf H1Rk-Ang-2 for Reduced Vegf189 Binding

BiSAb-VEGF H1RK-ANG-2 was screened for binding to VEGF189 in an ELISA format. 96-well half well maxisorp plates were coated with 25 μl of 2 μg/mL human VEGF189 (R&D Systems) diluted in PBS without Ca++ or Mg++ and refrigerated overnight. Plates were decanted, then blocked for 1.5 hours at 37° C. with 180 μl of Blocking Buffer containing 3% BSA (Sigma, Cat #A-3059) and 0.1% Tween-20 in 1×PBS. Plates were washed 3 times with 1×PBS containing 0.1% Tween-20. 50 μl of 6.7 nM and serial dilutions of BiSAb-VEGF H1RK-ANG-2, G6-31 (positive control) and BS3Ab-r347-Ang2 (negative control) in blocking buffer were added in duplicate and incubated at 37° C. for 1 hour. Plates were washed 3 times with wash buffer, then 50 μl of 1:5000 goat anti-human HRP IgG H+L (Jackson Immunoresearch) was added to each well and incubated at room temperature for 1 hour. Plates were developed by adding 50 μl of TMB solution (KPL) to each well, then stopping the reaction with 50 μl of 1M phosphoric acid. Plates were read at 450 nm using a microplate reader. FIG. 14 shows representative results for BiSAb-VEGF H1RK-ANG-2. BiSAb-VEGF H1RK-ANG-2 showed 5 fold lower binding to VEGF189 compared to the positive control G6-31 (EC50 0.057 nM vs 0.0096 nM).

Example 9—Functional Assays to Determine Potency of Vegf-Ang2 Bispecific Antibodies BiSAb-VEGF H1RK-ANG-2 were screened in functional bioassays to determine ability to reduce pVEGFR2 and pTie2 in cell lines with human, mouse and cyno receptors. Ad293-HuVEGFR2 (Cl. E2), Hek293-Tie2, Ad293-mu-VEGFR2-muAng2 cells (Cl. D10), Ad293-cynoVEGFR2-cynoAng2 cells (Cl. SB5) and Ad293-cynoTie2 cells (Cl. D12) were generated from stable transfections. Cells were seeded at subconfluency in 96-well poly-D-Lysine tissue culture plates (Costar, Tewksbury, Mass.) with 100 μl DMEM+10% FBS (Life Technologies, Carlsbad, Calif.) and incubated overnight at 37° C. and 5% CO2. The next day, media was aspirated and replaced with 50 μl starvation media (DMEM+0.2% FBS+0.1% BSA) and cells were returned to the incubator overnight. At 24 hours, media was aspirated and 2660 nM (2× concentration) antibodies, BiSAb-VEGF H1RK-ANG-2 and BS3Ab-HPV-r347 negative control were serially diluted in serum free DMEM+0.1% BSA and added in duplicate to the plate for 30 minutes at 37° C. Then, 50 µl of 12 µg/ml human, mouse (R&D Systems) or cyno Ang2 (in-house preparation)+20 nM of human, mouse (Peprotech, Rocky Hill, N.J.), or cyno (in-house preparation) VEGF (4×) mixed 1:1 was then added to the wells and incubated at 4° C. for 30 minutes. Plates were then incubated at 37° C. for an additional 7 minutes. Plates were decanted and wells lysed with 55 µl ice cold RIPA lysis buffer (Boston BioProducts, Boston, Mass.) containing protease and phosphatase inhibitors (Life Technologies, Carlsbad, Calif.). Human, cyno and murine pVEGFR2 were detected using pVEGFR2 whole cell lysate kits (Meso Scale Diagnostics, Rockville, Md.).

Human and cyno pTie2 was determined using a protocol developed using the Meso Scale Diagnostics (MSD) platform. MSD high bind plates were coated overnight with 2 µg/ml of Tie2 antibody clone 16 (Abcam, Cambridge, Mass.). The next day, plates were washed with tris buffered saline (TBS) only and blocked with 3% MSD Blocker A+0.05% Tween 20 (Sigma, St Louis, Mo.) in TBS for 1 hour at room temperature with rotary shaking. Plates were washed with TBS+0.05% Tween 20 and lysates were added to plate, and then incubated for 1 hour at room temperature with rotary shaking. Plates were washed and 1 µg/ml of anti-human Tie2 antibody (AF2720, R&D Systems, Minneapolis, Minn.) was added for 1 hour at room temperature with rotary shaking. Plates were washed, then 1 µg/ml sulfo-tag goat anti-rabbit secondary antibody (MSD, Rockville, Md.) was added to the plates for 1 hour at room temperature with rotary shaking. Plates were washed, Read Buffer T (MSD, Rockville, Md.) was added, then plates read immediately using a Sector Imager 6000 (MSD, Rockville, Md.).

Murine pTie2 was determined using a protocol developed using the Meso Scale Diagnostics (MSD) platform. MSD streptavidin plates were blocked with 3% MSD Blocker A+0.05% Tween 20 (Sigma, St Louis, Mo.) in TBS for 1 hour at room temperature with rotary shaking. Plates were washed with TBS+0.05% Tween 20 and then 25 µl/well of 2 µg/ml Biotin anti-mouse Tie2 antibody (Biolegend #124006) in blocking buffer was incubated for 1 hour at room temperature with rotary shaking. Plates were decanted and washed 3 times. Then, 25 µl/well of lysate was added per well in duplicate and incubated at room temperature for 2 hours on a plate shaker. Plates were washed, then 25 µl of sulfo-tag PY20 (MSD) was added per well and incubated for 1 hour at room temperature on a plate shaker. Plates were washed, then 150 µl of 2×MSD read buffer T was added and plates were read immediately using a Sector Imager 6000 (MSD, Rockville, Md.).

Percent phosphorylation for pTie2 and pVEGFR2 was calculated by the formula: [average RLU (test sample)/average RLU (no antibody)]*100. Representative results are shown in Table 3. BiSAb-VEGF H1RK-ANG-2 potently reduced human, mouse and cyno pVEGFR2 and pTie2 showing that both arms are functional in the bispecific format. The Anti-ANG-2 activity of BiSAb-VEGF H1RK-ANG-2 showed remarkably greater activity when compared to the ANG-2 antibody (MEDI3617) used to the make the scFV anti-ANG-2 of BiSAb-VEGF H1RK-ANG-2.

TABLE 3

| | Ad293-HuVEGFR2 cells (Cl. E2) | Hek293-Tie2 cells | MuVEGFR2-MuTie2 Cells (Cl. D10) | | Cyno VEGFR2-Cyno Tie2 Cells (Cl. SB5) | Ad293-CynoTie2 cells (Cl. D12) |
|---|---|---|---|---|---|---|
| | Hu pVEGFR2 $EC_{50}$ (nM) | Hu pTie2 $EC_{50}$ (nM) | Mu pVEGFR2 $EC_{50}$ (nM) | Mu pTie2 $EC_{50}$ (nM) | Cyno pVEGFR2 $EC_{50}$ (nM) | Cyno pTie2 $EC_{50}$ (nM) |
| Molecule | | | | | | |
| BS3Ab-VEGF H1RK-Ang2 | 0.087 | 2.29 | 5.95 | 12.16 | 0.131 | 3.47 |
| H1RK | 0.071 | not tested | not tested | not tested | 0.099 | not tested |
| Controls | | | | | | |
| B20-4.1 | not tested | not tested | 26.25 | not tested | 4.25 | not tested |
| Ang2 antibody | not tested | 2.65 | not tested | 137 | not tested | 33.17 |
| BS3Ab-HPV-r347 (−) control | N/A | N/A | N/A | N/A | N/A | N/A |

Example 10—In Vivo Activity of Bisab-Vegf H1Rk-Ang-2

BiSAb-VEGF H1RK-ANG-2 was tested in vivo for efficacy in a 786-0 renal cell carcinoma and a BxPC3 pancreatic carcinoma model which included casting of the BxPC3 tumors to illustrate anti-angiogenesis within the tumor compartment. In addition, retinal vasculogenesis models were performed to further demonstrate the activity of BiSAb-VEGF H1RK-ANG-2. Even more, a model of thrombocytopenia was performed in mice to determine if less toxicity occurred with BiSAb-VEGF H1RK-ANG-2 compared to an anti-VEGF positive control antibody (G6-31) that binds to all isoforms of VEGF. Finally, renal pathology was evaluated.

Figure 15:
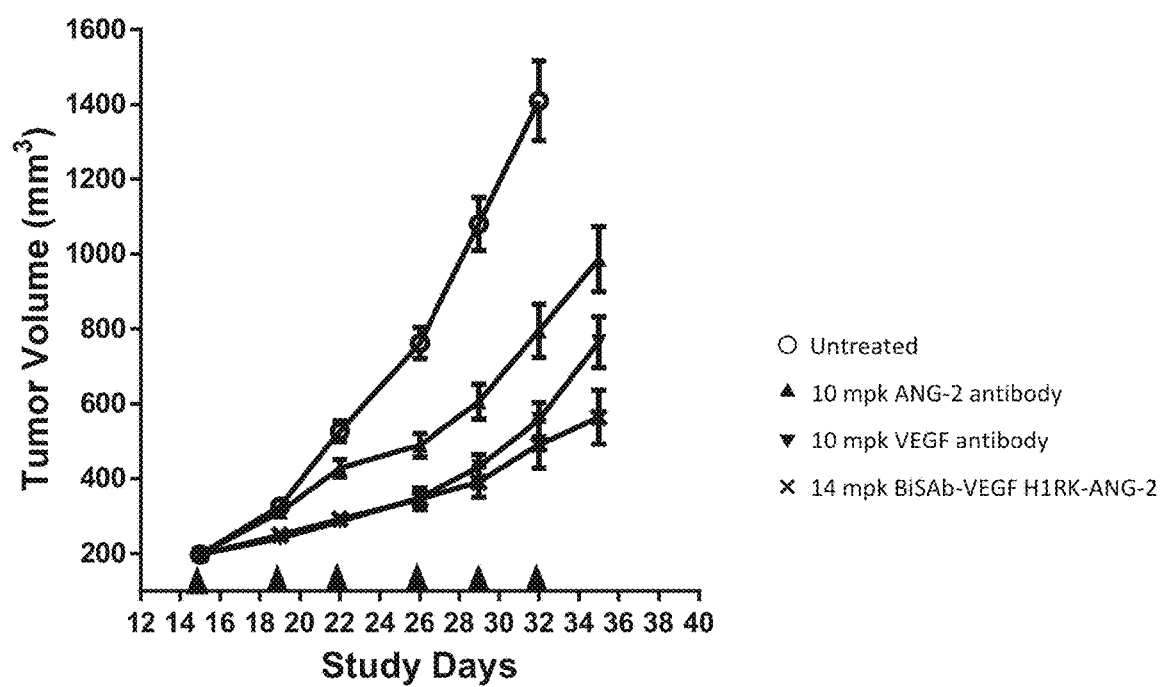
FIG. 15 depicts representative data showing reduction in tumor volume in the presence of the bispecific antibody BiSAb-VEGF H1RK-ANG-2 in a 786-0 renal cell carcinoma model.

For the 786-0 renal cell carcinoma model, tumor fragments from a human renal cancer cell line, 786-0, were implanted subcutaneously into the right flank of nude mice. After tumor volume reached approximately 200 mm³, dosing was initiated. Mice were treated twice per week for a total of 6 doses (triangles on axis). Doses were normalized based on molecular weight. BiSAb-VEGF H1RK-ANG-2 was more effective at reducing tumor growth compared to either the ANG-2 antibody (MEDI3617) or the VEGF antibody (Avastin®) alone. P-value=0.03 as determined by one-way ANOVA analysis Graphpad Prism version 5.01 (San Diego Calif.). Representative data are shown in FIG. 15.

Figure 16:
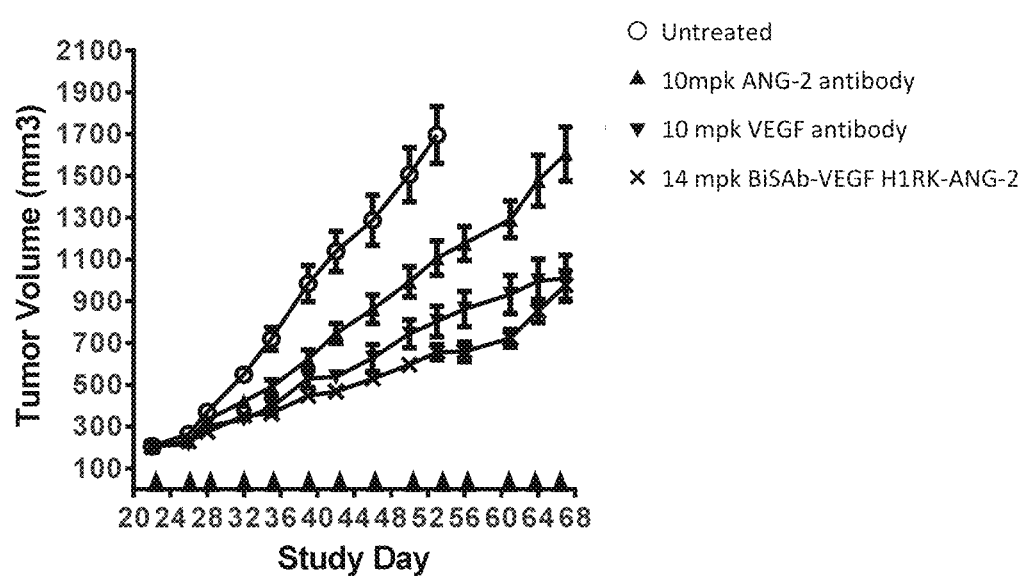
FIG. 16 depicts representative data showing reduction in tumor volume in the presence of the bispecific antibody BiSAb-VEGF H1RK-ANG-2 in a BxPC3 pancreatic carcinoma model.

For the BxPC3 pancreatic carcinoma model, BxPC3 tumor fragments were implanted subcutaneously into the right flank of female SCID mice. After tumor volume reached approximately 200 mm³, dosing was initiated. Mice were dosed twice per week for a total of 6 doses (triangles on axis). Doses were normalized based on molecular weight. BiSAb-VEGF H1RK-ANG-2 was more effective at reducing tumor growth compared to either the ANG-2 antibody (MEDI3617) or the VEGF antibody (Avastin®) alone. P-value=0.02, as determined by one-way ANOVA analysis Graphpad Prism version 5.01 (San Diego Calif.). Representative data are shown in FIG. 16.

Figure 17A:
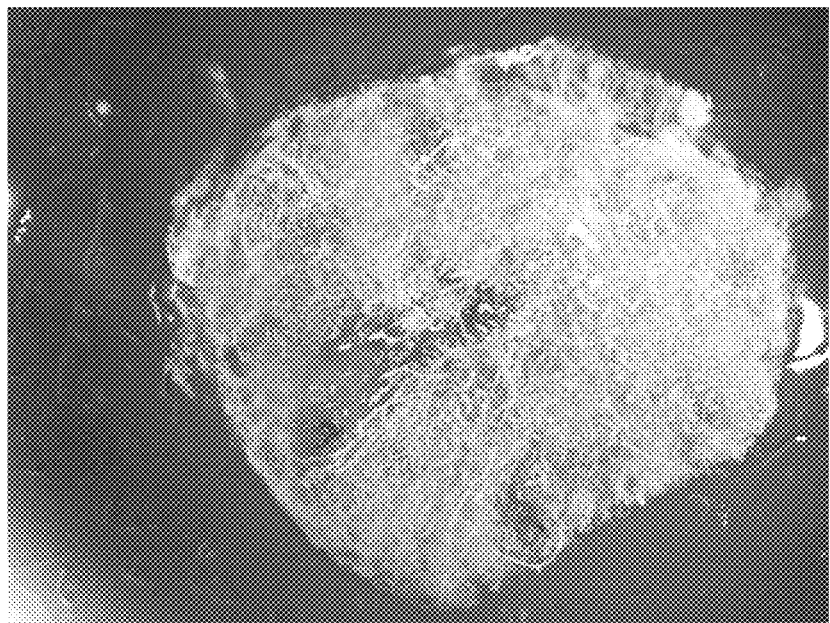
FIG. 17A depicts representative data showing vasculogenesis without the presence of the bispecific antibody BiSAb-VEGF H1RK-ANG-2.
Figure 17B:
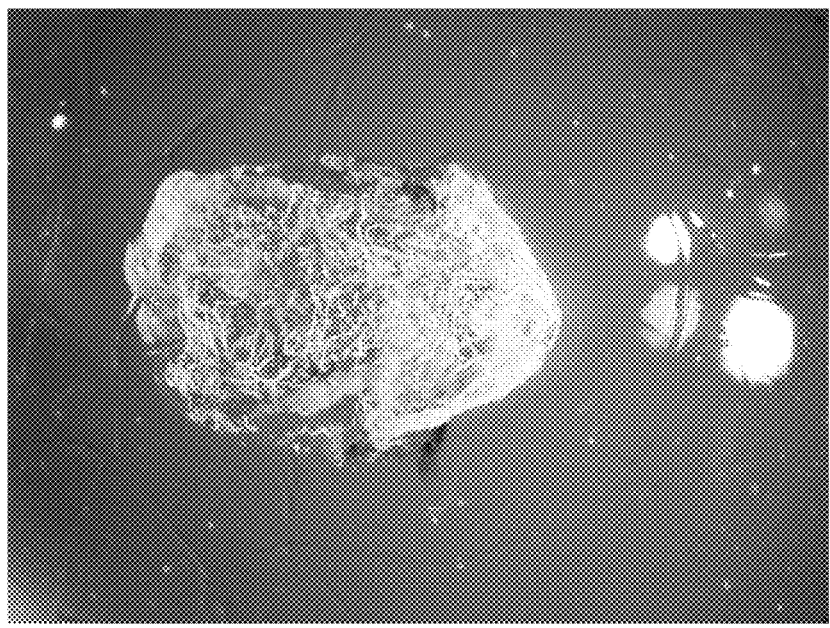
FIG. 17B depicts representative data showing vasculogenesis in the presence of the bispecific antibody BiSAb-VEGF H1RK-ANG-2.

In addition to tumor volume, tumor vasculature was evaluated using tumors from BxPC3 pancreatic carcinoma model work. Mice were dosed with heparin to prevent blood clotting 15 minutes prior to euthanasia. A solution of 0.1 mM sodium nitroprusside was perfused at a rate of approximately 6 mL/min. Microfil MV-122 was prepared by mixing 8 mL of latex, 10 mL of diluent and 900 uL of cure. After the mixture settled (approximately 1 minute) it was perfused at a rate of 2 mL/min until a total volume of 17 mL was administered. After 60-90 minutes the tumor was dissected and immersed in 10% NBF for 24 hours. The sample was then transferred through an ethanol gradient (25% ETOH/PBS, 50% ETOH/PBS, 75% ETOH/PBS, 95% ETOH, and then 100% ETOH) for 24 hours each gradient level. After the final incubation the sample was immersed in methyl salicylate to clear the dehydrated tumor sample before imaging by light microscopy. Tumor vasculature was reduced in mice with BiSAb-VEGF H1RK-ANG-2. Representative data are shown in FIG. 17.

In addition to the models described above, BiSAb-VEGF H1RK-ANG-2 was evaluated in a retinal angiogenesis model. Using this model CD1 mice were intraparatoneally dosed at birth, days 1, 3, and 5. At day 8 the mice were anesthetized and were infused with fluorescein-labeled dextran. Eyes were removed and fixed with 10% formalin before preparation of flat mounts. Flat mounts were examined by fluorescence microscopy.

Figure 18:
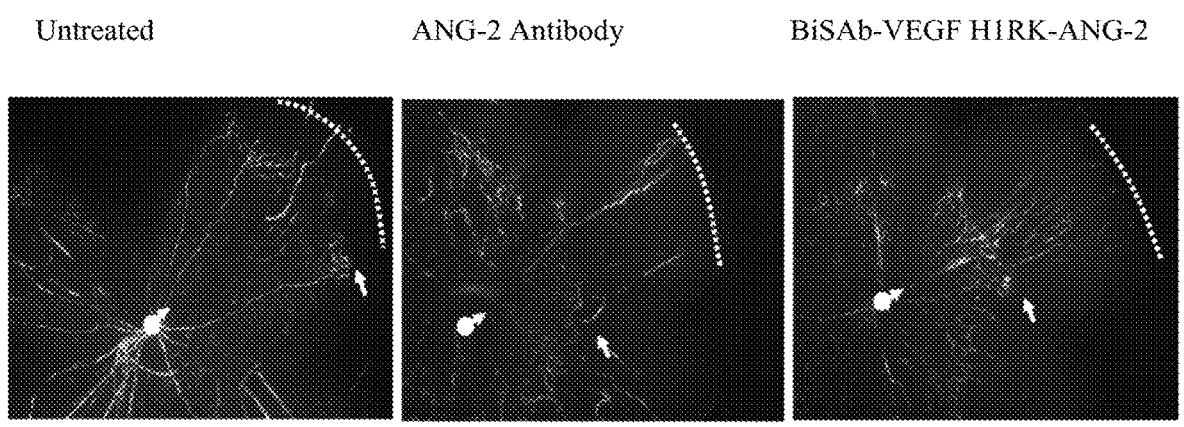
FIG. 18 depicts representative data showing reduction of the vessel migration (arrow) towards the periphery of the retina (dashed line) in the presence of the bispecific antibody BiSAb-VEGF H1RK-ANG-2. 4× magnification.

Neonatal retinal angiogenesis is comprised of two processes, namely, vessel migration from the optic nerve (FIG. 18 dot-arrow) to the edge of the retina and branching. BiSAb-VEGF H1RK-ANG-2 demonstrated reduced vessel migration compared to the extent of migration without BiSAb-VEGF H1RK-ANG-2 present. Representative results are shown in FIG. 18. BiSAb-VEGF H1RK-ANG-2 demonstrated reduced vessel branching compare to the extent of branching without BiSAb-VEGF H1RK-ANG-2 present. Representative data are shown in FIG. 19.

For the thrombocytopenia model, a method was adopted from Meyer et al. (J Thromb Haemost 7:171-81, 2009). Briefly FC gamma receptor 2A transgenic mice, 8-16 weeks old were injected with premixed VEGF165, 0.6 units heparin, and antibody into the lateral tail vein. Mice were then observed for behavioural signs of distress and scored as: (−) stopped and moved constantly from corner to corner, breathing normal, (+) signs of lethargy, stopped and moved in longer duration, breathing shallow, (++) very lethargic, stopped moving, staying in mostly one side of the box, breathing deeply, (+++) sever thrombotic event-twitching and twirling, (++++) death. BiSAb-VEGF H1RK-ANG-2 had reduced thrombocytopenia as compared to the anti-VEGF control (G6-31). Representative data are shown in Table 4.

TABLE 4

|  | Observations | Score |
| --- | --- | --- |
| Anti-VEGF* + VEGF165 + 0.6 units Heparin | Labored breathing, twitching and twirling | +++ |
| BiSAb-VEGF H1RK-ANG-2 + 0.6 units Heparin | Stopped and moved with glimpses of slowing down but recovers quickly, breathes normally. | −/+ |

*Anti-VEGF binds all isoforms of VEGF

Figure 20A:
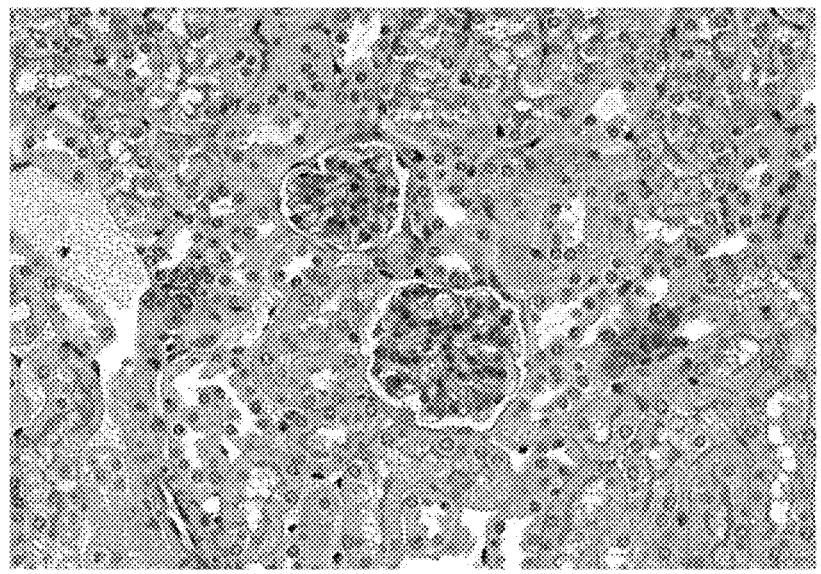
FIG. 20A depicts representative data showing renal pathology without the presence of the anti-VEGF antibody and the bispecific antibody BiSAb-VEGF H1RK-ANG-2.
Figure 20B:
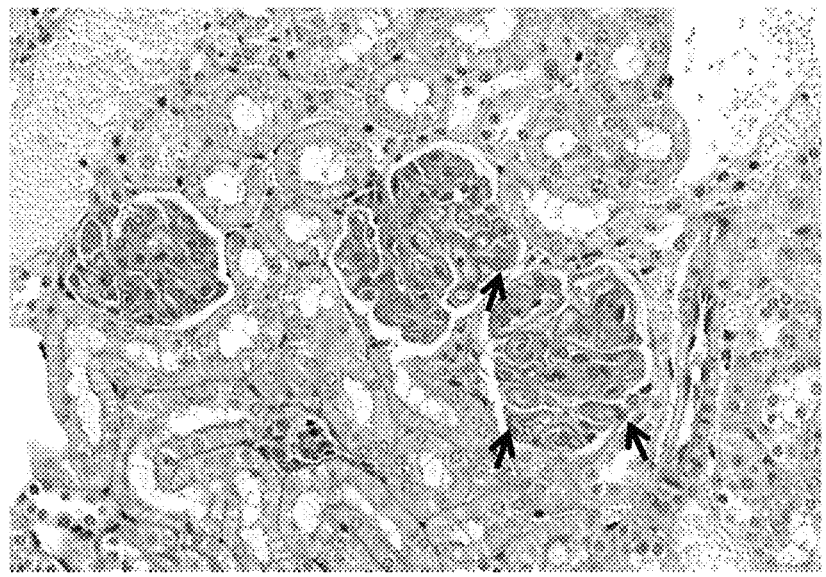
FIG. 20B depicts representative data showing renal pathology data in the presence of the anti-VEGF antibody.
Figure 20C:
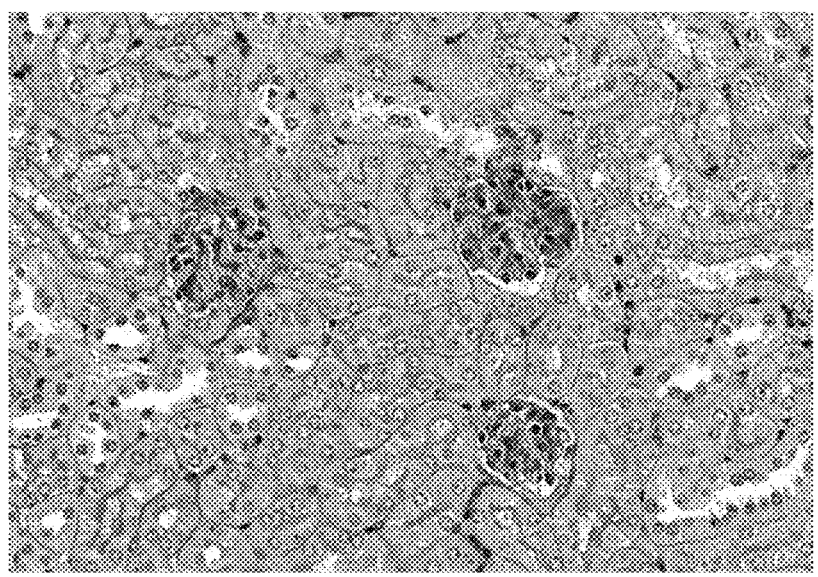
FIG. 20C depicts representative data showing reduction in renal pathology in the presence of the bispecific BiSAb-VEGF H1RK-ANG-2 present.

Kidneys from four animals per group were examined by staining via Periodic acid-Schiff (PAS). The PAS staining was used to examine kidney pathology after 14 doses of the treatments. There was increased mesangial matrix and thickened capillary loops (arrows) in the anti-VEGF (G6-31) treated animals compared to the BiSAb-VEGF H1RK-ANG-2. Representative are shown in Table 5 and FIGS. 20A-20C.

TABLE 5

| Pathology | Untreated | Anti-VEGF | BiSAb-VEGF H1RK-ANG-2 |
| --- | --- | --- | --- |
| Increased mesangial matrix | 0 | 2.75 | 0 |
| Thickened capillary loops | 0 | 2 | 0 |

Grade 0 = absent,
Grade 1 = minimal,
Grade 2 = Mild,
Grade 3 = Moderate,
Grade 4 = Severe,
Grade 5 = Very Severe

INCORPORATION BY REFERENCE

All references cited herein, including patents, patent applications, papers, text books, and the like, and the references cited therein, to the extent that they are not already, are hereby incorporated herein by reference in their entireties for all purposes.

EQUIVALENTS

The foregoing written specification is considered to be sufficient to enable one skilled in the art to practice the embodiments. It will be appreciated, however, that no matter how detailed the foregoing may appear in text, the embodiments may be practiced in many ways and the claims include any equivalents thereof.

The invention claimed is:

1. A nucleic acid molecule comprising polynucleotides encoding a bispecific antibody, said bispecific antibody comprising a first binding domain comprising heavy chain complementarity determining regions 1-3 (HCDR1, HCDR2, and HCDR3) and light chain complementarity determining regions 1-3 (LCDR1, LCDR2, and LCDR3), wherein the first binding domain HCDR1, HCDR2, and HCDR3 and LCDR1, LCDR2, and LCDR3 comprise SEQ ID NOs: 17-22, respectively, and a second binding domain comprising an HCDR1, HCDR2, and HCDR3 and an LCDR1, LCDR2, and LCDR3, wherein the second binding domain HCDR1, HCDR2, and HCDR3 and LCDR1, LCDR2, and LCDR3 comprise SEQ ID NOs: 23-28, respectively.

2. A vector comprising the nucleic acid molecule of claim 1.

3. A cell comprising the vector of claim 2.

4. A method of making a bispecific antibody comprising culturing a cell comprising the vector of claim 2.

* * * * *